US012673214B2

(12) United States Patent
Makansi

(10) Patent No.: US 12,673,214 B2
(45) Date of Patent: Jul. 7, 2026

(54) LESS INVASIVE AND IMPROVED PERIPHERAL NERVE STIMULATORS FOR OBSTRUCTIVE SLEEP APNEA AND OTHER APPLICATIONS

(71) Applicant: StimAire, Inc., Tucson, AZ (US)

(72) Inventor: Tarek Makansi, Tucson, AZ (US)

(73) Assignee: StimAire, Inc., Tucson, AZ (US)

( * ) Notice: Subject to any disclaimer, the term of this patent is extended or adjusted under 35 U.S.C. 154(b) by 911 days.

(21) Appl. No.: 17/799,086

(22) PCT Filed: Feb. 10, 2021

(86) PCT No.: PCT/US2021/017512
§ 371 (c)(1),
(2) Date: Aug. 11, 2022

(87) PCT Pub. No.: WO2021/163228
PCT Pub. Date: Aug. 19, 2021

(65) Prior Publication Data
US 2023/0355997 A1 Nov. 9, 2023

Related U.S. Application Data

(60) Provisional application No. 62/972,829, filed on Feb. 11, 2020, provisional application No. 62/972,823, (Continued)

(51) Int. Cl.
*A61N 2/00* (2006.01)
*A61N 2/02* (2006.01)
(Continued)

(52) U.S. Cl.
CPC .............. *A61N 2/004* (2013.01); *A61N 2/02* (2013.01); *H02J 7/855* (2026.01); *H02J 50/12* (2016.02); *H02J 2105/46* (2026.01)

(58) Field of Classification Search
CPC ........... A61N 1/37205; A61N 1/37223; A61N 1/3787; A61N 2/00; A61N 2/004; A61N 2/006; A61N 2/008; A61N 2/02
See application file for complete search history.

(56) References Cited

U.S. PATENT DOCUMENTS

| 6,240,318 B1 | 5/2001 | Phillips |
| 2012/0022609 A1 | 1/2012 | Bolea et al. |
| | (Continued) | |

FOREIGN PATENT DOCUMENTS

| JP | 2014528263 A | 10/2014 |
| JP | 2019531855 A | 11/2019 |
| | (Continued) | |

OTHER PUBLICATIONS

Office Action issued in Japanese Patent Application No. 2022-548431, issued on Nov. 1, 2024, 8 pages including 5 pages of English Translation.
(Continued)

*Primary Examiner* — Carrie R Dorna
(74) *Attorney, Agent, or Firm* — Dorsey & Whitney LLP

(57) ABSTRACT

Neural stimulator systems with an external magnetic coil to produce changing magnetic fields is applied on the neck, in conjunction with one or more tiny injectable objects that concentrates the induced electric or magnetic field to the hypoglossal nerve and protects the user by limiting and charge-balancing the output. Additional and non-invasive neural stimulator systems apply alternating current at one skin electrode and receive oppositely rectified currents at two other skin electrodes.

15 Claims, 22 Drawing Sheets

Related U.S. Application Data filed on Feb. 11, 2020, provisional application No. 62/972,815, filed on Feb. 11, 2020.

(51) Int. Cl.

| | |
|---|---|
| *H02J 7/00* | (2006.01) |
| *H02J 50/12* | (2016.01) |
| *H02J 105/46* | (2026.01) |

(56) References Cited

U.S. PATENT DOCUMENTS

| | | |
|---|---|---|
| 2013/0018248 A1 | 1/2013 | Hurezan |
| 2013/0085560 A1 | 4/2013 | Mashiach |
| 2014/0039579 A1 | 2/2014 | Mashiach et al. |
| 2017/0072199 A1* | 3/2017 | Biele ................... A61N 1/0553 |
| 2018/0078761 A1 | 3/2018 | Bolea et al. |
| 2018/0126159 A1 | 5/2018 | Meadows et al. |
| 2019/0275328 A1* | 9/2019 | Zitnik ................ A61N 1/37205 |
| 2019/0321636 A1 | 10/2019 | Law et al. |

FOREIGN PATENT DOCUMENTS

| | | | | |
|---|---|---|---|---|
| JP | 2023513247 A | 3/2023 | | |
| WO | 2013046044 A2 | 4/2013 | | |
| WO | WO2018071906 | * | 4/2018 | ........... A61N 1/3787 |
| WO | WO-2018071906 A1 | * | 4/2018 | ........... A61N 1/3787 |
| WO | 2019140404 A1 | 7/2019 | | |
| WO | 2021163228 A1 | 8/2021 | | |

OTHER PUBLICATIONS

First Examination Report issued in Australian Patent Application No. 2021218682, issued on Sep. 4, 2025, 3 pages.

Extended European Search Report issued in European Patent Application No. 21754220.8, mailed on Dec. 22, 2023, 7 pages.

International Preliminary Report on Patentability issued in International Patent Application PCT/US2021/017512, mailed on Aug. 25, 2022, 12 pages.

International Search Report and Written Opinion dated Jun. 15, 2021 for PCT Application No. PCT/US2021/017512, 20 pages.

First Office Action issued in Canadian Application No. 3166004, mailed on Jan. 14, 2026, 5 pages.

* cited by examiner

LESS INVASIVE AND IMPROVED PERIPHERAL NERVE STIMULATORS FOR OBSTRUCTIVE SLEEP APNEA AND OTHER APPLICATIONS

CROSS-REFERENCE TO RELATED APPLICATIONS

This application National Stage Application of International Application No. PCT/US2021/017512, filed on Feb. 10, 2021, which in turn claims the benefit of priority to U.S. Provisional Patent Application Ser. No. 62/972,815, filed on Feb. 11, 2020, U.S. Provisional Patent Application Ser. No. 62/972,823, filed on Feb. 11, 2020, U.S. Provisional Patent Application Ser. No. 62/972,829, filed on Feb. 11, 2020, and U.S. Provisional Patent Application Ser. No. 63/069,072, filed on Aug. 23, 2020, each of which is hereby incorporated by reference in its entirety.

BACKGROUND

The human and mammal bodies use electrical signals to achieve sensory input, muscle movements, thoughts, and memory. Over time, these signals are also responsible for neural plasticity, which includes general wiring, rewiring, and de-wiring of the brain. The electrical signals are represented in the mind and body as potentials (voltages) created by ions, not electrons. However, these ion-transported signals can be initiated, negated, or altered by electric fields that originate from inside or outside the body. By Faraday's law of electromagnetics, these electric fields can be generated from changing magnetic fields, hence, the name "magnetic stimulation". Because these signals are initiated from outside the body, magnetic stimulation can be a non-invasive means for altering or improving of almost all bodily and mental functions.

The signals inside the body are "action potentials" that are pulse-frequency modulated, meaning that the pulse rate is related to the intensity of the sensed input, muscular energy, or neuronal message. The shapes of individual pulses are largely the same throughout, having a pulse width of about 1 millisecond and some undershoot after the main pulse. The pulse height is approximately 70 millivolts for sensory signals and somewhat larger for muscle activation. Pulses for the heart, digestive system, and may other organs have other unique characteristics. For the most part, the signals all look the similar when viewed on an oscilloscope: a "pulse train" wherein the pulse repetition frequency is indicative of the magnitude of the transmitted signal. The absence of a pulse train can also cause a reaction, explaining why amputees still feel parts of the body that no longer exist.

The meaning of the individual signal to the body's nervous system is dependent on where pulse train appears. The brain consists of regions that handle various neural functions and provide input for thoughtful and sensory processing. The peripheral nervous system contains axons that serve as communication channels and repeaters between the sensory nerve endings and the spinal cord and ultimately the brain. The neuromuscular system also consists of axons that communicate in the opposite direction allowing the brain to cause various muscle motions. Axons are grouped together into multi-channel peripheral nerves as they approach the spinal cord or the brain. Some axons are myelinated to increase the propagation rate of the pulse trains to and from the extremities of the body.

Neural stimulation devices strive to create, negate, or alter these naturally-occurring pulse trains in a targeted location to achieve a beneficial result. This may include blocking or stimulation of neural activity. Ultimately, an electric field is required at the location that causes ions to appropriately to trigger an action potential that then can propagate unassisted through the nervous system to its destination. This electric field may be induced rather than generated directly. For example, traditional magnetic stimulation first creates a time-varying magnetic field from a coil of wire, which in turn generates an electric field per Faraday's law. When this electric field is induced on a portion of the neurosensory system, or the neuromuscular system, or brain's neural network, it can alter that system by depolarizing or hyperpolarizing the pulse trains that naturally exist or by inserting a pulse train that does not exist. In the nervous system and the brain, these pulse trains run continuously; only the frequency changes to convey the intensity information.

The prior-art neural stimulation devices fall into three categories: (1) magnetic stimulation wherein changing magnetic fields produced by a coil outside the body generate electric fields inside the body that alters the natural nerve or neuronal signals, (2) skin-electrode stimulation wherein electrodes are placed on the skin and cause current to flow into the body from one electrode to the other, and (3) implanted wire stimulation wherein electrodes implanted at a targeted location and connected by wires to a driver circuit possibly also implanted in another part of the body. Inspire Medical's hypoglossal nerve stimulator is an example of implanted wire stimulation. Transcranial Magnetic Stimulation (TMS) is an example of magnetic stimulation. Transcutaneous Electrical Neural Stimulation (TENS) is an example of skin-electrode stimulation.

Magnetic stimulation is non-invasive, but unpredictable and low in efficacy because the stimulation is not targeted and the mechanism of action is not understood. Regarding medical treatment, magnetic stimulation has achieved regulatory approval for treating major depression, neuropathic pain, and headaches. According to clinicaltrials.gov, 1165 clinical studies have been or are being performed with "magnetic stimulation" by 427 unique sponsors to understand its effect on 450 different conditions. Magnetic stimulation may include a single external coil, multiple external coils for better targeting such as US2012/0302821A1 and also wearable coils such as U.S. Pat. No. 9,072,891B1 and US2010/0160712A1.

Skin-electrode stimulation is non-invasive, but untargeted and uncontrollable because the electrical current follows multiple paths with varying intensity. Transcutaneous Electrical Nerve Stimulation (TENS) devices are approved for very few indications and efficacy is generally low. Many TENS devices advise applying the highest intensity electricity that the patient can tolerate to maximize efficacy. The electricity flowing from the skin electrodes must pass through nerve endings in the skin before ultimately are reaching the intended target, a peripheral nerve or muscle. The electric shock sensation or paresthesias from these nerve endings has non-therapeutic adverse effects of pain and discomfort from an electric shock sensation. Even after the patient dials up the maximum tolerable electricity at the skin, the current density at the target nerve is often insufficient to be of much therapeutic use.

Implanted wire stimulation is highly targeted, but also highly invasive and unstable due to electrode movement from wire-tugging during bodily motions. Infection is also a disadvantage especially if the driver circuit is not implanted.

SUMMARY

The embodiments described herein addresses certain limitations of prior-art implanted wire stimulation for obstructive sleep apnea (OSA), replacing implanted wires with a wearable and injectable connected together wirelessly. Additional embodiments described herein address certain limitations of prior skin-electrode stimulation by reducing or eliminating the electric shock sensation. Hence, these embodiments are expected to greatly advance the state of the art for the benefit of mankind.

In one or more embodiments, a wireless neuromodulation system is provided to allow wireless stimulation to eliminate surgery and reduce the complexity to one injection at each desired location of stimulation, and/or make the injectable piece so small that it will not move around over time in an active human body. These objectives are achieved with these embodiments and are applied to treating Obstructive Sleep Apnea (OSA) via stimulation of the hypoglossal nerve. These embodiments improve the breath sensing capability over the prior art while retaining the ability to measure heart rate and blood oxygen levels with a plethysmography sensor. These embodiments also include additional components in the injectable that safely limit the voltage applied to the tissue and insure zero or near-zero net charge to prevent electrode corrosion while maintaining injectability in an even smaller needle as compared to the prior art. These embodiments also provide a full functionality in the wearable for OSA therapy while maintaining a lightweight form factor and sufficiently long battery life as compared to the prior art. This full functionality permits a full treatment protocol to implement the therapy by a physician and an assistant. The end result is a treatment for OSA and other conditions that is low cost and yet provides the full function of much larger and more invasive prior-art devices that are surgically implanted.

In one or more additional embodiments, a novel TENS system is provided to eliminate or reduce the electric shock sensation at nerve endings near the skin, and permit stronger electricity to reach the target nerve, and thereby increase efficacy of multiple therapies involving TENS. These objectives are achieved with these additional embodiments. The reduction of the electric shock sensation improves the acceptability of TENS for the patient over the prior art. This reduction also increases the maximum tolerable stimulation intensity, and hence is expected to increase the efficacy of TENS over the prior art for many treatments.

The neural stimulator embodiments for OSA described herein may use an external coil to produce changing magnetic fields outside the body, in conjunction with one or more tiny injectable objects that concentrates the field to a highly-targeted location. These systems also add a driver circuit for the magnetic coil that allows for high voltage and fast pulses in the coil, while requiring low-voltage power supply that could be a wearable battery. The coil and driver circuit and battery are also small enough to be easily wearable, and may include a plethysmograph sensor to gather patient data on heart rate and oxygen saturation level. An injectable elongate device is placed inside the body adjacent to the hypoglossal nerve, and this device has circuits that rectify the received alternating-current signal, limit the output voltage to a safe level, and reverse the flow of current after stimulation to charge-balance the area. A second wearable device that senses breathing, including the periods of inhalation and exhalation, may be included to more effectively provide stimulation at the optimal times or optimal amplitudes or optimal times and amplitudes.

Miniaturization of the magnetic field generator may be achieved using (1) an efficient driver circuit that enables hundreds or thousands of volts in the coil from a low voltage battery, (2) an injectable field concentrator that targets the stimulation to an area as small as microns if desired, and/or (3) a fast rise time in the current of the coil that induces a large electric field to evoke an action potential.

Some of the systems disclosed herein use an electronic circuit to drive the stimulator coil or coils by stimulating a pulse as multiple decaying cycles of a resonance of the stimulator coil combined with a capacitor. Once the decay of the resonance is complete, the circuit remains turned off until the desired time for the next pulse.

By using this approach, the inductive energy of the stimulating coil is recycled through the capacitor, and therefore not wasted on each cycle. In addition, the voltage across the capacitor can reach hundreds or thousands of volts even when the supply voltage is very low. This high voltage internal to the capacitor is then used to rapidly change the current in the stimulating coil for the next pulse. The recycling of the inductive energy also allows for the stimulating coil to have more turns, and therefore needs less current flow to create the same magnetic field strength. The preferred embodiment can create the needed magnetic field pulses with power supply in the range of 3 to 45 volts DC and an average current flow from the supply of 0.001 to 0.1 amps for treating OSA.

In some embodiments of the systems, in addition to enabling a smaller injectable, the healthcare provider or the user/wearer still has the flexibility to set the signal parameters as needed for effective stimulation of the hypoglossal nerve. The wearable provides an interface that allows healthcare provider to titrate the stimulation intensity and burst frequency, and then fix this level for subsequent use by the user/wearer.

In one embodiment, the injectable also includes a rectifying diode, a charge-balancing capacitor, a voltage-limiting Zener diode, and a timing resistor. The tissue-exposed surfaces of the elongate injectable may comprise a material selected from a group consisting of a metal for the electrodes and an insulator encapsulation. The metal surface may be copper, tungsten, chromium, steel, stainless steel, nickel, nichrome, titanium, gold, silver, brass, platinum, iridium, platinum-iridium or any alloy thereof. The insulator surface may comprise PTFE, nylon, silicone, polyethylene, polyurethane, latex, polyimide, BoPET, or any combination thereof. The elongate injectable may be configured for placement adjacent to the hypoglossal nerve. The elongate injectable may comprise a cylindrical shape with a diameter and a length, wherein the diameter may be less than the length. The elongate device may be injected into the body through a guiding tube, such as a needle of a syringe or other introducing needle. The magnetic field generator may comprise a coil, the coil comprising one or more coil windings of wire, possibly stranded wire wherein the strands are insulated from one another. The magnetic field generator may be connected in parallel with a capacitor and configured such that a stimulation signal may be generated by, result from, or be defined by a portion in time of a resonance between the coil and the capacitor. The parallel capacitor and coil may be configured to be activated by a DC power supply or battery on one side and a switch to ground on the other side, wherein a time period between the switch closing and the switch opening builds up the electrical current in the coil, and the time after switch opening presents the decaying resonance that induces a burst of stimulation pulses. The switch may be a combination of a transistor and a rectifier and a switching action may be configured to occur by turning the transistor on or off by applying a voltage to a gate or a base of the transistor. The magnetic field generator may comprise a stimulator coil, the stimulator coil may comprise a material with high magnetic permeability configured to contain the fringe fields. The material with high magnetic permeability may comprise rigid or flexible ferrite, steel, or iron. The coil may further comprise a conducting ferromagnetic material that reduces the amplitude of subsequent resonant pulses relative to the prior pulses. The material may comprise iron, cobalt, nickel, steel, or an alloy or other combination thereof. The one or more coil windings may be in a plane or in multiple adjacent planes. The one or more coil windings may comprise magnet wire or bundled strands of magnet wire, each strand insulated or not. The one or more coil windings may comprise metal deposited on a layered substrate. The substrate may be rigid, and may optionally comprise FR-4 glass-reinforced epoxy laminate, glass, or hard plastic. In other embodiments, the substrate may be flexible. The flexible substrate may comprise polyimide, BoPET, polyethylene, polyurethane, nylon, or PTFE. The system may further comprise one or more of a microprocessor, rechargeable battery, disposable battery, user interface, physician interface, nurse interface, data storage, and network or wired connection.

The network or wired interface may be configured to receive information from another sensor providing a signal that indicates physical body movements related to breathing. This sensor may comprise a piezoelectric disk facing a center pivot and interface circuitry to the microprocessor's analog-to-digital converter.

The wearable may include a plethysmograph sensor to gather information on the patient's health such as oxygen saturation level and/or heart rate.

In another embodiment, a method of treating OSA is provided, comprising identifying an OSA patient, injecting the patient with one or more elongate devices adjacent to the hypoglossal nerve, placing a wearable magnetic field generator against skin surface near the injection site, and applying a magnetic field to generate therapeutic neural stimulation.

In still another embodiment, a treatment device is provided to introduce the injectable into the body, comprising a syringe or injector body or introducer, a sliding plunger or pushrod located in the syringe or injector body, a needle attached to the syringe or injector body possibly with a tip that can apply electrical stimulation like a nerve-block needle, and at least one discrete elongate injectable located in the syringe or injector body, wherein the syringe or injector body and needle restrain the orientation of the at least one elongate injectable, and wherein the elongate injectable comprises a resistor, capacitor, Zener diode, and a rectifying diode.

In another embodiment, a neuromodulation system is provided, comprising at least one elongate device with a length of less than fifteen millimeters and a transverse dimension to the length of less than two millimeters, configured for implantation adjacent or against the hypoglossal nerve, and a magnetic field generator that may be spaced apart from the elongate device, and configured to generate an induced voltage between a pair of electrodes of the elongate device. The at least one elongate device may be pre-loaded in an injection device and in a sealed sterile package. The magnetic field generator may further comprise a rechargeable battery or a disposable, non-rechargeable battery. The magnetic field generator may be located in a housing comprising a biocompatible adhesive. The housing may have a height relative to a skin surface at the location on the human body that may be less than three centimeters.

In another embodiment, a method of treating a patient is provided, comprising inserting at least one elongate injectable against or adjacent to the hypoglossal nerve, wherein the injectable has a length of less than fifteen millimeters and a transverse dimension to the length of less than two millimeters, positioning a magnetic field generator at a location spaced away from the at least one elongate injectable, and using the magnetic field generator to provide an induced voltage between a pair of electrodes on at least one elongate injectable. This treatment method may also include the use of an ultrasound imaging system to assist the healthcare provider in placing the injectable at the hypoglossal nerve. This treatment method may also include a device that applies electrical stimulation to the tip of the introducing needle to verify proximity to the hypoglossal nerve prior to placement.

In another embodiment, the field generator also contains or connects to sensors, including an oxygen saturation level sensor, a plethysmograph sensor, or connected to a breathing-motion sensor mounted on the chest or abdomen. The oxygen saturation sensor or the plethysmograph sensor may contain pairs of light-emitting diodes and photosensors that sense redness of the tissues or expansion and contraction of the tissues in response to breathing and heart beats, or both of these. These sensors may have their outputs processed, using analog or digital signal processing, or both, possibly including Fourier or other linear transformations, filtering, peak detectors, amplitude detectors, polarity detectors, or envelope detectors, to monitor body and health parameters like breathing rate, breathing duty cycle, distinguishing inhaling from exhaling, snoring, partial breathing obstructions or hypopneas, full breathing obstructions or apneas, heart rate, blood pressure, breathing effectiveness, and blood oxygen levels. Information processed from these sensors may be used to determine stimulation turn-on and turn-off times, the amplitude of the stimulation, the specific or general health of the user, the effectiveness of the stimulation, or be gathered as useful general information for later processing. This information may be communicated from the field generator to a secure database, directly or through an intermediate base station.

In an additional set of embodiments, stimulation of a muscle or peripheral nerve is accomplished without requiring an injectable inside the body, and also reduces or eliminates the electric shock sensation of the prior-art TENS systems. In these embodiments, at least one stimulating electrode is placed on the skin directly above the target muscle or peripheral nerve, and at least two oppositely rectified return electrodes are placed on the skin at remote locations from the center electrode. In these embodiments, the center electrode applies alternating current of a frequency that alternates too fast to be felt by the nerve endings underneath it. The two return electrodes receive oppositely rectified polarities of the alternating current, each polarity directed by a diode. In addition, the surface area of each return electrode is large enough such that the current density flowing through the nerve endings at those locations is insufficient to cause pain or discomfort.

In one embodiment, a TENS system is provided using an alternating current generator, two diodes, one center skin electrode, and two return skin electrodes. This embodiment provides TENS therapy at the muscle or peripheral nerve under the center electrode while reducing or eliminating the electric shock sensation by directing rapidly alternating current and the center electrode and low-density current at the return electrodes.

In another embodiment, a treatment method for pain is described, by applying the center electrode to the nerves in the spinal cord for treating central pain.

In another embodiment, a treatment method for stimulating the median nerve is described for treating peripheral pain or carpal tunnel syndrome.

In another embodiment, a treatment method for migraine headaches is described by applying the center electrode stimulation to the supra-orbital nerve on the forehead.

In another embodiment, a treatment method for OSA is described by applying the center electrode to the hypoglossal nerve underneath the tongue.

In one embodiment, a neuromodulation system for obstructive sleep apnea is provided, comprising an elongate device configured for injection about the hypoglossal nerve, the at least one elongate device comprising a stimulating electrode, a return electrode, an elongated receiver coil, a first diode, a second Zener diode, a resistor, and a capacitor, and wherein the at least one elongate device does not contain a battery, a wearable device comprising a field-generating coil connected to a capacitor and configured together to freely resonate during repetitive stimulations of the hypoglossal nerve, wherein the elongate device is configured so that a voltage applied to the stimulating electrode is configured to be rectified by one or both diodes, to be limited by the Zener diode, and to average to zero or near zero before the start of the next free resonance. The wearable device may contain at least one button battery, which may be rechargeable or not rechargeable. The wearable device may be configured to allow adjustment of an amplitude of stimulation by setting an initial electrical current flowing in the field-generating coil prior to the free resonance. The setting of the initial electrical current of the wearable device may be based on the length of time that the field-generating coil is connected between a power supply and a ground. The first diode, the second Zener diode, the resistor, the capacitor and any interconnections therebetween may be coated with a moisture barrier with thickness between 5 and 50 microns, such as Parylene or Parylene C. The first diode, the second Zener diode, the resistor, the capacitor and any interconnections therebetween may be housed inside of a tube, which may comprise Polyimide or PEEK for example, and wherein any empty or vacant space in the tube may be filled with epoxy, including biocompatible epoxy. The stimulating and return electrodes may comprise a biocompatible metal, such as platinum, iridium, or an alloy of platinum and iridium, for example. The elongate device may further comprises a tether attached to the elongate device at a location spaced apart from the stimulating electrode and configured for removability. The tether may comprise a suture string, which may comprise a polyester, polypropylene, ultrahigh molecular weight polyethylene, or a combination material thereof. The suture string may comprises an absorbable synthetic material. The wearable device may be configured to adjust the amplitude in preset increments, which may optionally comprise a series of fixed percentage increases from an initial muscle-twitch threshold level. The elongate device may comprise a half wave rectifier, a full wave rectifier, or a center-tapped full wave rectifier, for example. The wearable device may be configured to provide an adjustable repetition rate of free resonances. The neuromodulation system may further comprise an introducer needle, wherein the elongate device is located inside the introducer needle. The elongate device may be one of at least two elongate devices inside the introducer needle. The introducer needle may be electrically insulated except at a tip of the introducer needle, and the tip of the introducer needle may be configured to be electrically connected to a stimulation device configured to assist placement of the elongate device adjacent to a nerve.

In another embodiment, a sensor for sensing breathing motion is provided, comprising a housing or pouch, a piezoelectric disk, a support disk, and a pivot therebetween contained in the pouch, wherein the support disk is located on a first side of the pouch configured for contact against a body of a user and wherein the piezoelectric disk is located on a second side of the pouch opposite the support disk, and is configured to be strapped toward the body. The sensor may further comprise an instrumented breathing belt strap, adhesive tape strap or an adhesive bandage strap, for example. The piezoelectric disk may be configured to be strapped with a waistband of a garment. The sensor may be electrically connected by a connector to a neuromodulation system, the neuromodulation system comprising an elongate device configured for injection about the hypoglossal nerve, the at least one elongate device comprising a stimulating electrode, a return electrode, an elongated receiver coil, a first diode, a second Zener diode, a resistor, and a capacitor; and wherein the at least one elongate device does not contain a battery, and a wearable device comprising a field-generating coil connected to a capacitor and configured together to freely resonate during repetitive stimulations of the hypoglossal nerve, wherein the elongate device is configured so that a voltage applied to the stimulating electrode is configured to be rectified by one or both diodes, to be limited by the Zener diode, and to average to zero or near zero before the start of the next free resonance. The connector may be a wire and/or a wireless link. The sensor may be configured to transmit a sensor output of the sensor as an analog signal and/or as a digital signal. The sensor output of the sensor is connected to a series resistor, which in turn is connected to an analog-to-digital converter. A resistance of the series resistor may be selected to have an R*C time constant of 0.3 or between 0.1 and 0.6 seconds, where C is the capacitance of the piezoelectric disk, R is the sum of the series resistance and the load resistance of the analog-to-digital converter circuit.

In another variation, a neuromodulation system is provided, comprising at least one surface stimulating electrode configured to apply alternating current and two surface return electrodes, configured to receive oppositely rectified components of the alternating current. The system may further comprise a diode configured to perform the rectification. A frequency of the alternating current may be selected to minimize or prevent electric shock sensation at its location on the body, and may be 1, 10, 100, or 1000 Kilohertz or any frequency therebetween, for example. An electrical contact area of the return electrodes may be sized to reduce high current density and electric shock sensation at their locations on the body. An absolute value of an amplitude of the oppositely rectified current components at each return electrode may be configured to be balanced by a balancer. The balancer may be configured to insert a series resistance, adjust a return electrode contact area, insert a bias voltage in the alternating current of the stimulating electrode, or any combination thereof. The neuromodulation system may further comprise a microprocessor configured to sense an imbalance and control the balancer. The alternating current may be a periodic waveform modulated by a slowly decreasing, a slowly increasing, or a constant amplitude multiplier. The periodic wave may be a sine wave, a square wave, or a triangular wave, for example. The stimulating electrode may be configured for placement over a peripheral nerve and does not penetrate the skin. The neuromodulation system may be configured to modulate a supraorbital nerve to treat pain from migraine headaches. The peripheral nerve may be a peripheral portion of the hypoglossal nerve and wherein the neuromodulation system is configured to treat obstructive sleep apnea, a median nerve and wherein the neuromodulation system is configured to treat carpal tunnel syndrome, an ulnar nerve and wherein the neuromodulation system is configured to treat pain from cubital tunnel syndrome. The neuromodulation system may be configured to treat peripheral pain corresponding to the peripheral nerve. The stimulating electrode is configured for placement over the spinal cord, or inside the mouth to treat obstructive sleep apnea, for example. The elongate device may be one of at least two elongate devices of the neuromodulation system. The wearable device may be one of at least two wearable devices of the neuromodulation system.

In still another example, a method of performing neuromodulation is provided, comprising placing a neuromodulation device about a nerve, the neuromodulation device comprising a stimulating electrode and two return electrodes, applying alternating current with the stimulating electrode and receiving oppositely rectified components of the alternating current. The method may further comprise rectifying the alternating current with a diode located in the neuromodulation device. The method may further comprise selecting a frequency of the alternating current in a range of 1 Hz to 1000 Hz to reduce paresthesia or shock sensation. The method may further comprise balancing an absolute value of an amplitude of the oppositely rectified current components at each return electrode. The balancing may be performed by inserting a series resistance, adjusting a return electrode contact area, and/or inserting a bias voltage in the alternating current of the stimulating electrode. The neuromodulation device further comprises a microprocessor configured to control the balancing. The alternating current may be a periodic waveform modulated by a slowly decreasing, a slowly increasing, or a constant amplitude multiplier. The periodic wave is a sine wave, square wave, or triangular wave. The nerve may be a peripheral nerve and wherein placing the neuromodulation device comprises non-invasively placing the neuromodulation device over the peripheral nerve against the skin. The peripheral nerve may be a supraorbital nerve and wherein the neuromodulation device is configured to treat migraine headaches. The peripheral nerve may be a peripheral portion of the hypoglossal nerve and wherein the neuromodulation device is configured or used to treat migraine headaches. The peripheral nerve may be a median nerve and wherein the neuromodulation device is configured to treat carpal tunnel syndrome, or the ulnar nerve and wherein the neuromodulation device is configured or used to treat cubital tunnel syndrome. The neuromodulation device may also be configured or used to treat peripheral pain. Placing the neuromodulation device may comprise positioning the stimulating electrode of the neuromodulation device over a spinal cord location, or inside a mouth of a patient to treat obstructive sleep apnea.

DETAILED DESCRIPTION

Figures 1A, 1B:
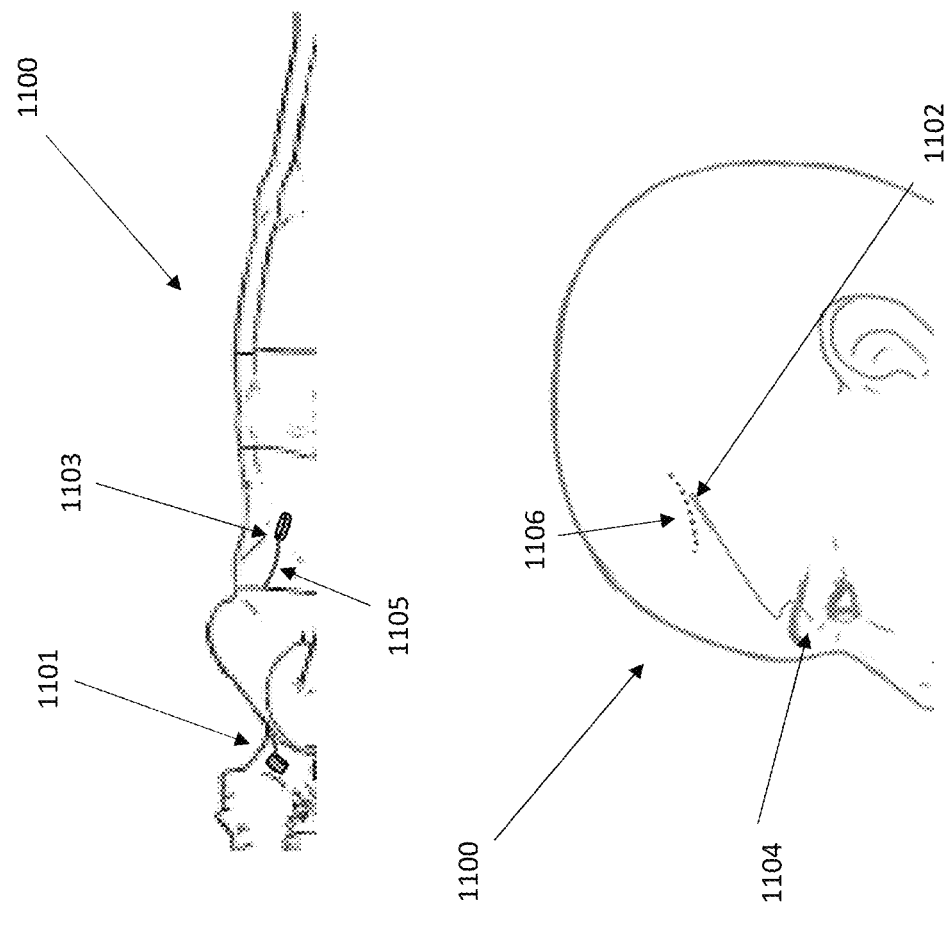
FIG. 1A is a graphical representation of a patient lying down and being treated for OSA with a wearable device mounted under the chin and a sensor that senses breathing motion mounted in the chest area.
FIG. 1B is a corresponding graphical representation of the patients head and neck showing the locations of the hypoglossal nerve and the injectable elongate device placed adjacent to it. A tether connected to the injectable device is partially outside the body.

FIG. 1A illustrates an exemplary system configured for neuromodulation therapy, including but not limited to treating OSA. Patient 1100 has a battery-powered wearable field generator 1101 affixed on the neck under the chin that activates an internal injectable, and breathing sensor 1103 affixed in the chest or abdomen area. Sensor 1103 communicates a signal that specifies breathing motion to wearable 1101 using a wire 1105. The wire 1105 may transmit the sensor output signal in either analog form or in digital form if an analog-to-digital converter is included. Without limitation, this wire could be replaced with a wireless link wherein a wireless transmitter at the sensor transmits the sensor output to the wearable. Wearable 1101 transmits magnetic energy via inductive coupling to an injectable receiver 1102 in FIG. 1B, which is placed via injection adjacent to the hypoglossal nerve 1106. The injectable 1102 may or may not have a tether 1104 attached to it to facilitate removability of the injectable.

In FIG. 1B, the device operates by injectable 1102 applying a train of neuromodulation pulses to the hypoglossal nerve from magnetic energy it receives from wearable 1101 which may or may not be enabled by sensor 1103 revealing the inhalation portion of the breathing cycle. OSA is caused by the patient's tongue being pulled into the airway and blocking airflow during the inhalation phases of breathing. Stimulation of the hypoglossal nerve activates the genioglossus muscles which protrude the tongue, clearing the airway for breathing, and treating OSA.

Wearable Description

Figure 2B:
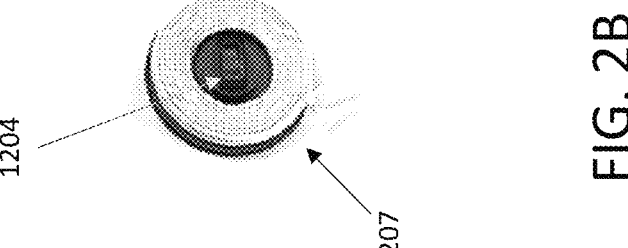
FIG. 2B is a perspective view of an exemplary plethysmograph sensor usable with the wearable field generator.
Figure 2A:
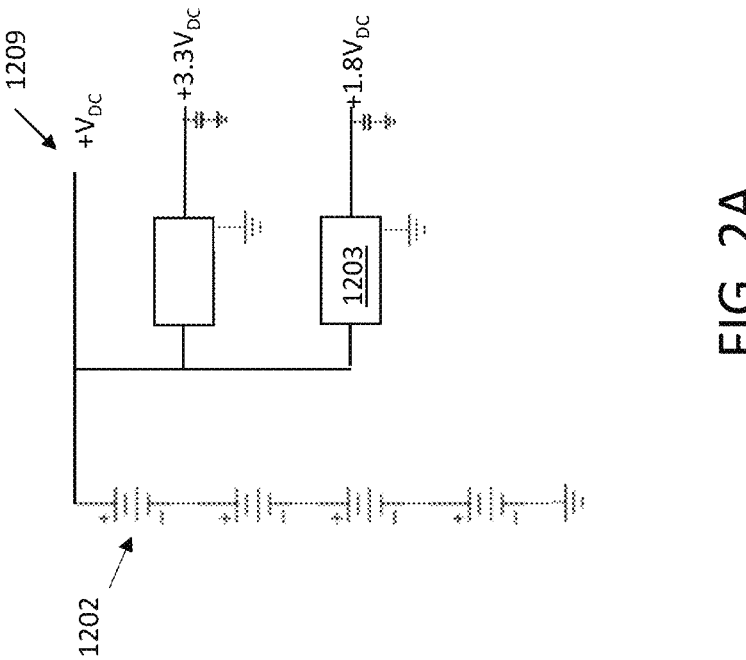
FIG. 2A is an electrical diagram of the power.
Figure 2C:
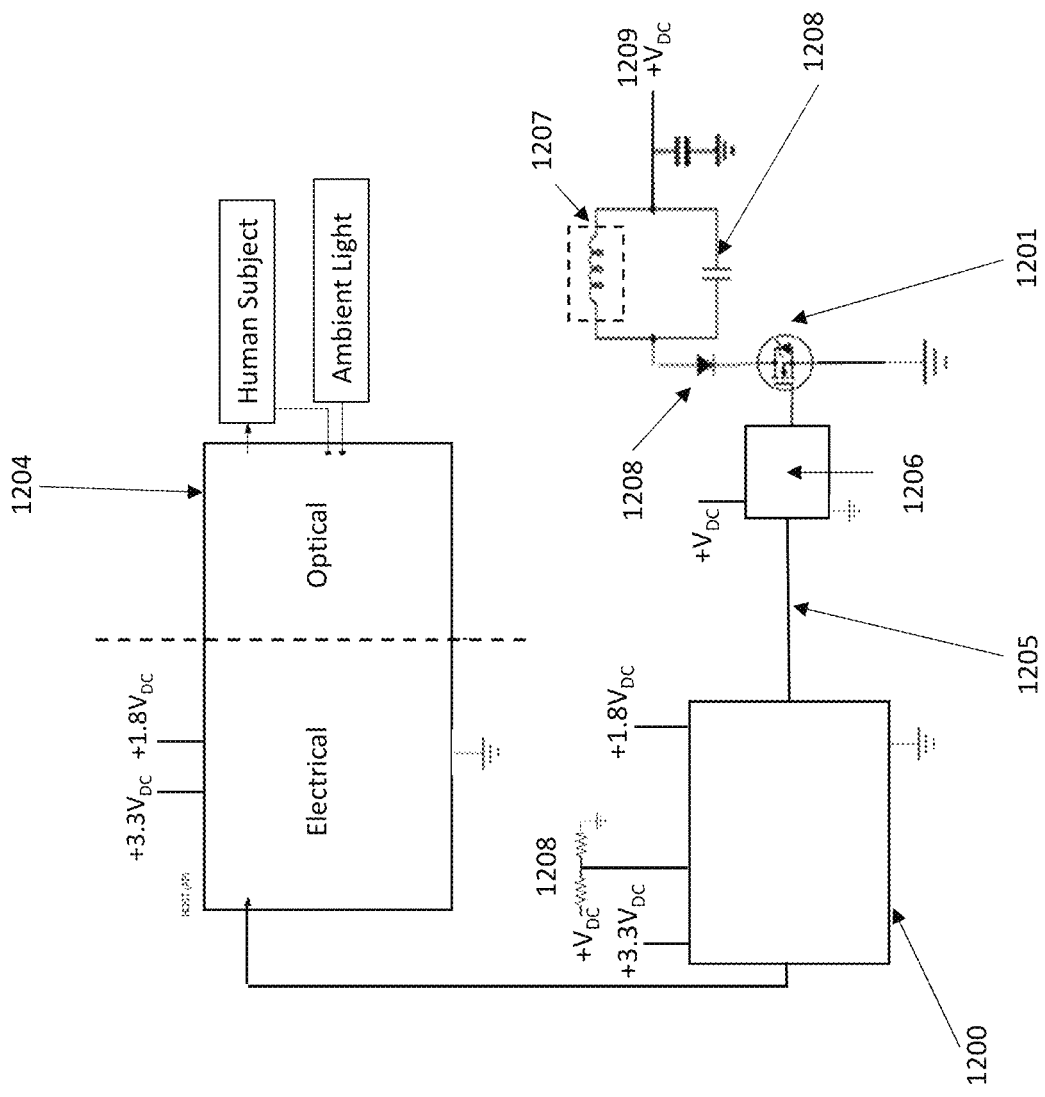
FIG. 2C.
Figures 3A, 3B, 3C:
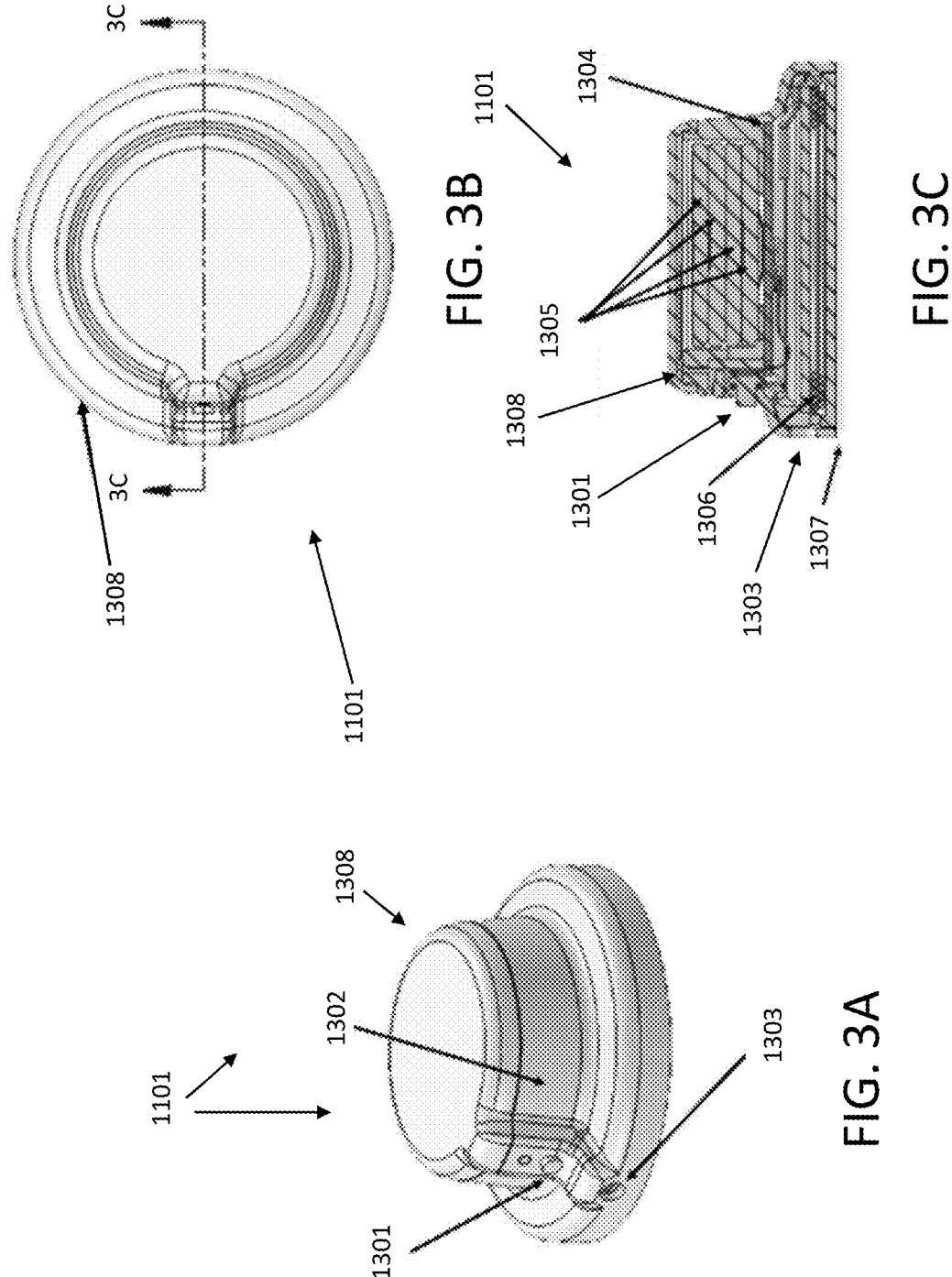
FIG. 3A is an isometric graphical representation of the wearable field generator.
FIG. 3B is a top-view graphical representation of the wearable field generator in in FIG. 3A.
FIG. 3C is a cross-sectional side view of the graphical representation of the wearable field generator in FIG. 3A.

The wearable 1101 has a physical appearance and construction as shown in FIGS. 3A to 3C and a schematic representation shown in FIG. 2C. The wearable is a lightweight device that adheres to the skin with biocompatible adhesive 1307 in FIG. 3C at the injection site and generates a magnetic field to activate the injectable for neuromodulation. The wearable has a 35 mm outer diameter 1308 in FIG. 3B and profile height of 15 mm as illustrated in FIG. 3C. In other variations, the outer diameter or maximum horizontal dimension may be in the range of 30 mm to 40 mm, 20 m to 50 mm or 10 mm to 40 mm, and the height may be in the range of 10 mm to 20 mm, 8 mm to 20 mm, or 5 mm to 20 mm. The major components of the wearable are the following: a circuit board 1304 in FIG. 3C comprising a microprocessor that controls the amplitude and timing of decaying free-resonance pulses to the field-generating coil 1306 and adjusts the settings from pushbutton 1301 sequences in FIG. 3A; said coil 1306 that generates a magnetic field to activate the injectable 1102 in FIG. 1B during neuromodulation; four 2016 button batteries 1305 in FIG. 3C or other button battery or battery pack to power the wearable for 10 hours or more. The circuit board may be a rigid or a flexible circuit board. These button batteries may be either rechargeable or disposable, and in other variations, the number of batteries may be in the range of 1 to 5, and may have a standard or a custom size/shape. A pushbutton 1301 in FIG. 3A to allow the user or physician to communicate with the wearable device; LED indicator 1302 to reveal the state of the wearable; a connector 1303 to the breathing sensor to allow the stimulation, optionally, to be on during inhale and off during exhale; a film of 3M 1315 double-sided, biocompatible adhesive 1307 in FIG. 3C or other adhesive to hold the wearable in position during sleep. The above components are provided in a housing 1308 that has a circular shape, but in other variations, a triangular, square, rectangular, oval or other shape may be provided. The cross-sectional profile of the housing 1308 in FIGS. 3A to 3C also comprise a number of angular surfaces, but in other variations, may comprise a dome-shape, which may reduce the risk of the device 1101 being caught on clothing and unintentionally pulled off the user's skin.

The schematic of the wearable's circuit shown in FIG. 2C is largely described in U.S. Pat. No. 10,744,339, which is hereby incorporated by reference in its entirety. A field generating coil 1207 in FIGS. 2B and 2C is connected in parallel with a resonant capacitor 1208 in FIG. 2C. This parallel combination is connected to the power supply 1209 in FIGS. 2A and 2C on one side and switch on the other side. The switch comprises a MOSFET transistor 1201 and a diode 1208 in FIG. 2C. The switch is turned on or off by a microprocessor 1200 driving a logic signal 1205 through a driver circuit 1206. A plethysmograph sensor 1204 optionally gathers data for the microprocessor regarding the patient's heart rate or blood oxygen saturation level. The power supply 1209 is generated from a series connection of one or more batteries 1202 in FIG. 2A, and this supply voltage may be stepped down to lower voltages by voltage converter 1203, as needed throughout the circuit.

Injectable Description

The injectable device is expected to be placed by the small introducer needle, as a smaller needle reduces the invasiveness of the injection procedure. Deeper nerves in the body need a larger diameter receiver coil in the injectable, and hence a lower gauge, larger diameter, needle to introduce the injectable into the body. In some variations, the introducer needle gauge size may be in the range of 12 gauge to 16 gauge to reach the deepest nerves up to 10-20 cm, 14 gauge to 18 gauge for medium depth nerves of 3-10 cm or 17 gauge to 22 gauge for the shallowest nerves of up to 3.0 cm. In each case, the diameter of the injectable's receiver coil is slightly less than the inner diameter of the needle gauge. Functionally, the injectable has a receiver coil that receives a pulse train of magnetic energy from the wearable and converts it to a pulse train of voltage signals to apply to the hypoglossal nerve or other target location for neuromodulation. By Faraday's law of induction, a small receiver coil can only receive a high frequency, alternating current. Hence, the remainder of the injectable's circuit converts high frequency alternating current into a train of voltage pulses of one polarity followed by a longer period of the opposite polarity for charge balancing.

Figures 5A, 5B, 5C:
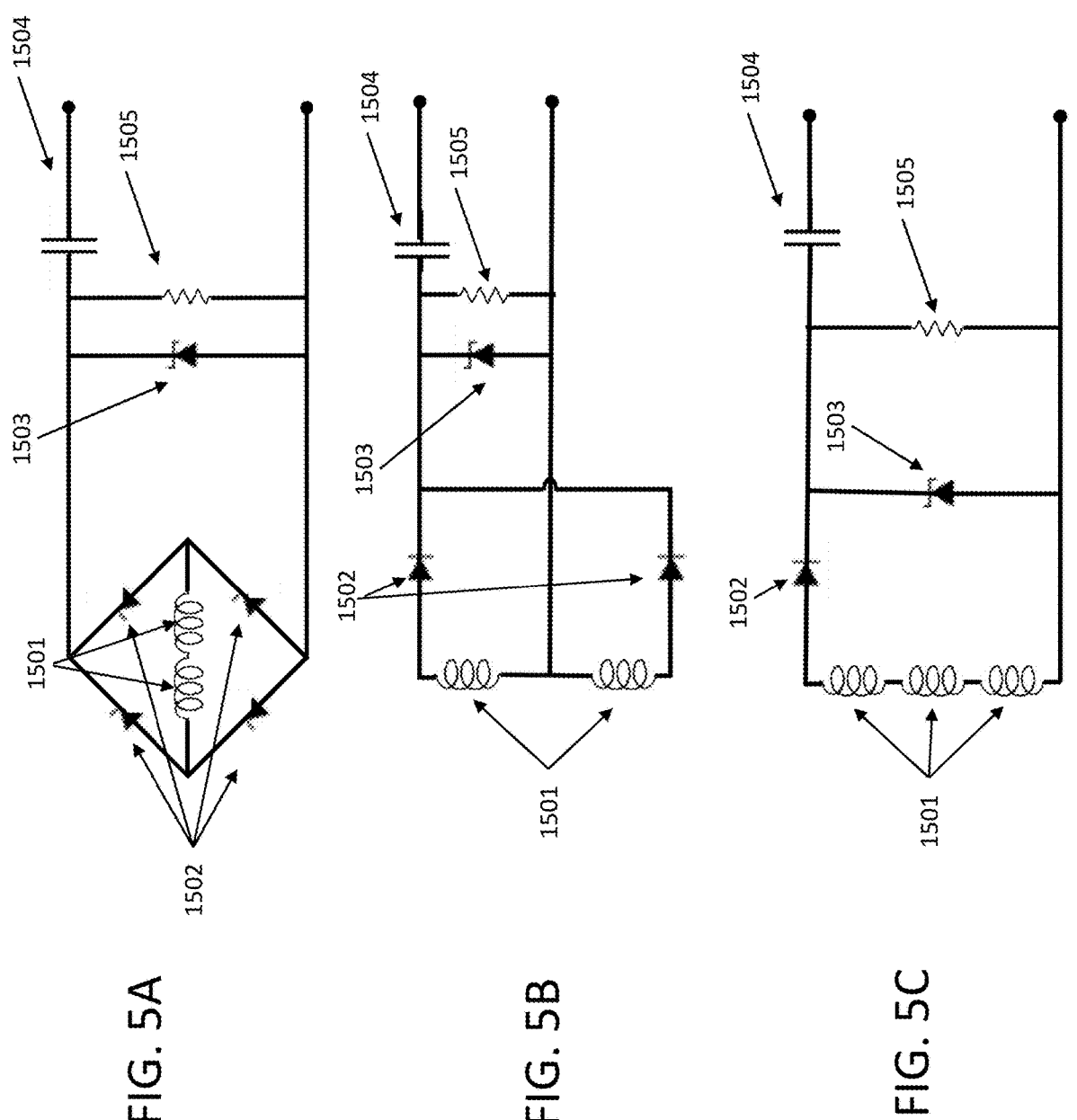
FIG. 5A is a schematic representation of the elongate injectable employing a full-wave rectifier.
FIG. 5B is a schematic representation of the elongate injectable employing a center-tapped full-wave rectifier.
FIG. 5C is a schematic representation of the elongate injectable employing a half-wave rectifier.
Figures 6A, 6B:
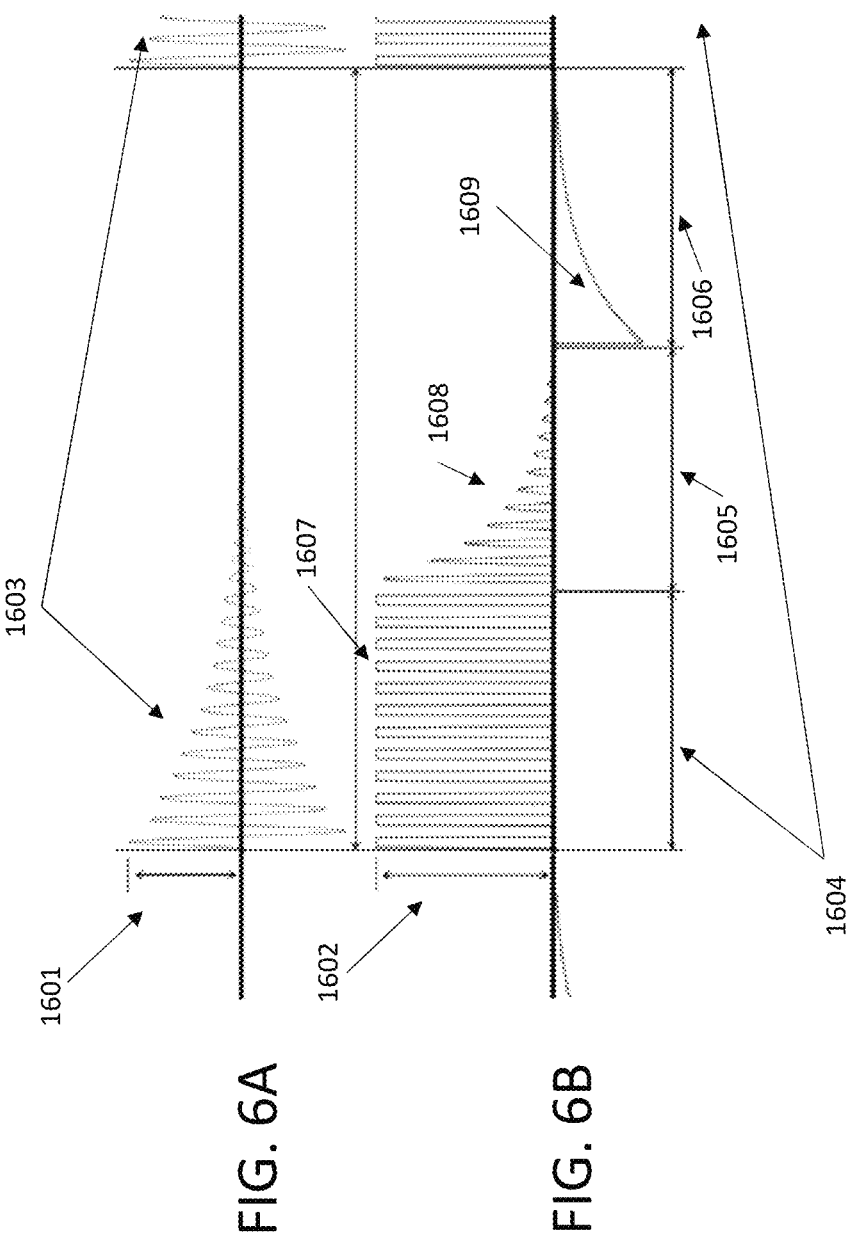
FIG. 6A shows a time series graphical representation of the voltage of the coil of the wearable field generator for a full stimulation burst of free resonance and the start of the next burst.
FIG. 6B shows a time series graphical representation of the corresponding voltage between the stimulating electrode and the return electrode in the elongate injectable.

The Injectable contains a circuit as indicated in one the schematics in FIGS. 5A to 5C, with an exemplary component layout and wiring diagram in FIGS. 7A to 7D, and an output waveform shown in FIG. 6B. FIGS. 5A to 5C show three exemplary schematics for the circuit of the injectable. The full wave rectifier option of FIG. 5A injects the most charge into the nerve for each free resonance cycle, but requires 8 passive components if the coils 1501 are considered in aggregate. The center-tapped, full wave rectifier option in FIG. 5B generates half the amplitude as FIG. 5A and requires 7 passive electronic components. The half-wave rectifier option of FIG. 5C also has half the charge injection as FIG. 5A, but only requires 5 passive electronic components. Because the circuit of FIG. 5C requires the fewest number of components and therefore can be fabricated with the smallest size. This circuit of FIG. 5C has two fewer diodes than FIG. 5A, but only delivers half of the charge injection per burst, as it only rectifies half of the wave.

The major components of the injectable shown in FIGS. 5C and 7A to 7D are as follows: custom receiver coil 1501 with a ferromagnetic core that intercepts the magnetic field generated by the wearable; a Schottky diode 1502 that rectifies the AC signal from the receiver coil into sinusoidal pulses shown in FIG. 6. A Zener diode 1503 that limits the voltage output of the injectable to 24 volts, as shown by the clipped pulses 1607 in FIG. 6B; a 0.22 µF capacitor that charge balances the output voltage to achieve zero net charge delivered to the tissue over time; a 10 KOhm resistor 1505 that defines the time constant of the charge re-balancing period 1609 indicated in FIG. 6B. These components are mounted on a printed circuit board 1705 in FIGS. 7B and 7C. Other embodiments use a Zener diode with a voltage limit of 2.4 to 5 volts for unmyelinated nerves or for backward compatibility to constant voltage limits of the prior art, or 5 to 24 volts to protect most tissues, or 24 to 100 volts for large-diameter nerves. Other embodiments use a capacitor between 0.01 and 0.22 µF for a faster balancing of charge for higher frequency stimulations or between 0.22 and 10 µF for lower frequency stimulation. Other embodiments use a resistor between 2 and 10 KOhm for higher frequency stimulation and still larger than tissue impedance of 0.5 to 2 KOhm, or use a resistor between 10 to 100 KOhm for lower frequency stimulations.

Figures 7A, 7B, 7C, 7D:
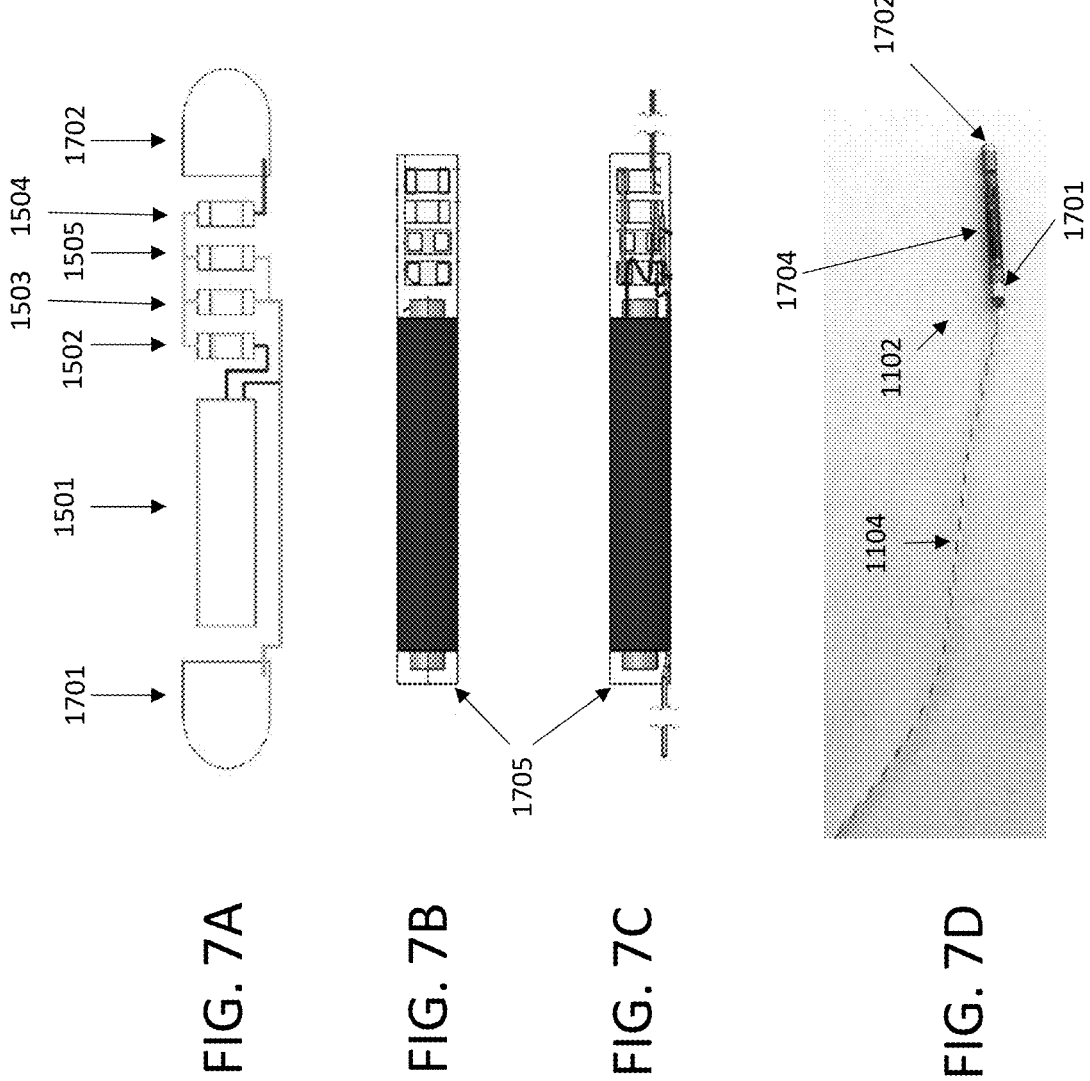
FIG. 7A is a graphical representation of the layout of the passive electronic components in the elongate injectable including the electrodes.
FIG. 7B is a graphical representation of the layout of the passive electronic components on a circuit board in the elongate injectable device.
FIG. 7C is a graphical representation of the layout of the passive electronic components on a circuit board in the elongate injectable and including the internal wiring.
FIG. 7D is a photographic representation of the elongate injectable ready to be packaged and sealed in a housing, and including a tether for removal after injection.

The electronics sub assembly shown in FIG. 7C is coated with Parylene C via vacuum deposition or coated with another type of Parylene or another moisture barrier coating, and then inserted into a biocompatible Polyimide tube 1704 in FIG. 7D. Without limitation, the tube could also made from PEEK, glass, or other biocompatible material or from a non-biocompatible material but coated with a biocompatible coating. This tube and coating serve as a moisture barrier preventing tissue fluids from entering and preventing exposure to non-biocompatible materials in the coated electronic components. FIG. 7C also illustrates how the components are connected together electrically to achieve the schematic representation in FIG. 5C. The electrode lead wires are spot welded to Platinum Iridium 90%-10% electrodes 1701 and 1702 shown in FIGS. 7A and 7C. Without limitation, the electrode could be comprised of another combination of platinum and iridium or other metal or metal alloy suitable for being inside the body and able to conduct electricity. The tube 1704 is filled with biocompatible epoxy or other epoxy for rigidity. Finally, the tether 1104 is routed through a hole in the return electrode, knotted, and epoxied into the tube. The tether could comprise suture string used for stitching wounds made from polyester, polypropylene, ultrahigh molecular weight polyethylene or a combination of these, or made from other biocompatible string. The tether could also be made from an absorbable synthetic material allowing the injectable to be optionally placed either temporarily or permanently inside the body.

Operation

The wearable transmits an oscillating, decaying magnetic field produced by free resonance behavior between a primary coil and a low-loss capacitor, as shown in FIG. 6A. The initial amplitude of this waveform 1601 in FIG. 6A is determined by the length of time the switch 1201 and 1208 are turned on in FIG. 2C by the microprocessor 1200. The longer this switch is turned on, the greater the initial current flowing in the field-generating coil 1207. Then, when the microprocessor turns off this switch, the coil 1207 resonates freely with capacitor 1208, and decays exponentially due to losses in these components as shown in 1603 of FIG. 6A. The turned-on time for the switch 1201 in FIG. 2C in this embodiment may be between 2 and 30 microseconds, with longer on-time required for deeper nerves and when the battery is drained. The on-time is adjusted to maintain the same level of stimulation for a given patient as the battery drains and its supply voltage decreases with sustained use. Other embodiments for deeper nerves and higher-inductance wearable coils may have an on-time of 30 microseconds to 1000 microseconds.

The injectable's secondary (receiver) coil picks up a portion of this magnetic field and generates an AC voltage per Faraday's law of induction. The voltage produced in the injectable is rectified by diode 1502 in FIG. 5C and presented to a high-pass filter comprising capacitor 1504 and resistor 1505 in FIG. 5C that insures charge balanced delivery of current to the stimulating electrode. The voltage generated by the receiver coil is also clipped at 24 volts, if necessary, by a Zener diode 1503 in FIG. 5C to protect the patient from excessive voltage and/or charge density. The resulting voltage presented to the electrodes of the injectable is shown in FIG. 6B. This circuit produces up to three different waveshapes for each free resonance burst 1603 from the transmission from wearable coil voltage in FIG. 6A. The first waveshape is in period 1604 in FIG. 6B wherein the voltage is half-wave rectified sinusoidal pulses clipped at amplitude 1607 or 24 volts by the Zener diode. In most embodiments, this first wave shape will not be present, as the 24 volt clipping function is for patient safety and not generally needed for therapy. The second waveshape period 1605 occurs when the amplitude from the receiver coil is naturally below the clip level 1607 or 24 volts, and comprises half-wave rectified sinusoidal pulses without clipping. The third waveshape period 1606 is the charge balancing period where the high-pass filter specifies that the net voltage on its output is zero over time, and consists primarily of a negative voltage that exponentially decays to zero.

The waveform of FIG. 6B comprises a series of rectified sinusoidal pulses. Peripheral nerves are stimulated extraneurally by the accumulation of charge near the wall of the nerve. The charge can accumulate by a sequence of unipolar voltage pulses shown in periods 1607 and 1608 in FIG. 6B or by a steady unipolar voltage common in the prior art.

The amplitude of stimulation is adjusted by the microprocessor 1200 in FIG. 2C by increasing or decreasing the on-time of the switch 1201 and 1208 prior to free resonance, and may be between 3 and 30 microseconds for this embodiment. The burst frequency of stimulation is adjusted microprocessor 1200 by increasing or decreasing the wait time between turn-ons of the switch, may be between 20 and 40 Hz for this embodiment. Patients report different sensations and discomfort levels with different burst frequencies, so having this range available is advantageous without compromising the effectiveness of the therapy. Other embodiments for other nerve stimulations may have burst frequencies between 5 and 20 Hz or between 40 and 1000 Hz, depending on the electrophysiology and the therapy. The effective pulse width of the stimulation is related to the decay time constant of the resonant circuit shown in periods 1607 and 1608 in FIG. 6B, and this parameter is fixed by the losses in the resonant circuit. For this embodiment, the effective pulse width is 90 microseconds; other embodiments may be 10 to 100 microseconds or 100 to 1000 microseconds. Hence, the amplitude and frequency of stimulation are readily adjustable by the microprocessor and these parameters can be set during titration of the device.

The microprocessor 1200 in FIG. 2C is configured to allow the user to adjust the amplitude and frequency of stimulation per Table 1 below.

| Mode | Initiated by | Indicated by | Function | Ended by |
|---|---|---|---|---|
| Intensity Setup | Hold button for 1 second | LED flashes quickly | Stimulation on for 1 sec. then not for 1 sec. Press button quickly once to increase intensity 1 level, twice quickly to decrease. (out of 20 levels). LED flashing will pause if change cannot be executed. | Hold button for 1-2 sec. to permanently set the intensity at current level. Device then turns off. |
| Frequency Setup | Hold button for 2 seconds | LED flashes slowly | Stimulation on for 1 sec. then off for 1 sec. Press button quickly once to increase intensity 1 level, twice quickly to decrease. (out of 10 levels). LED flashing will pause if change cannot be executed. | Hold button 1-2 sec. to permanently set the frequency at current level. Device then turns off. |
| Normal Operation | Press button quickly | LED flashes for 1 sec. then dark | Stimulation delivered during inhalation at set level, compensating for battery voltage droop. LED is on when inhalation is detected; dark otherwise, for the first three minutes. Press button quickly once to increase intensity | Hold button for 1-2 sec. to turn off device. |

-continued

| Mode | Initiated by | Indicated by | Function | Ended by |
|---|---|---|---|---|
| | | | 1 level, twice quickly to decrease. LED flash indicates change was successful. | |
| Off | Hold button for 1-2 seconds while on | LED on for 1 sec., then dark | Device completely off. | See Initiations |

The clinical use of the device is intended to be in the following sequence: the physician titrates in "Intensity Setup Mode" denoted by Row 1 of Table 1. The titration procedure is described in detail below. If the stimulation sensation is objectionable by the patient, then the "Frequency Setup Mode", denoted by Row 2 of Table 1, is used to find a more acceptable frequency of free-resonance stimulations. Then, titration is repeated. "Normal Operation" mode, denoted by Row 3 of Table 1 is used in the first three minutes to ensure the LED 1302 in FIG. 3A is blinking on with inhalation portion of the breathing cycle and this mode is restarted repeatedly until the breathing sensor is situated properly. "Normal Operation" mode, denoted by Row 3 in Table 1, is then used again beyond the first three minutes to provide therapy during sleep for the patient. To turn off the device for any reason, the sequence in Row 4 "Off" of Table 1 is invoked.

Figure 4:
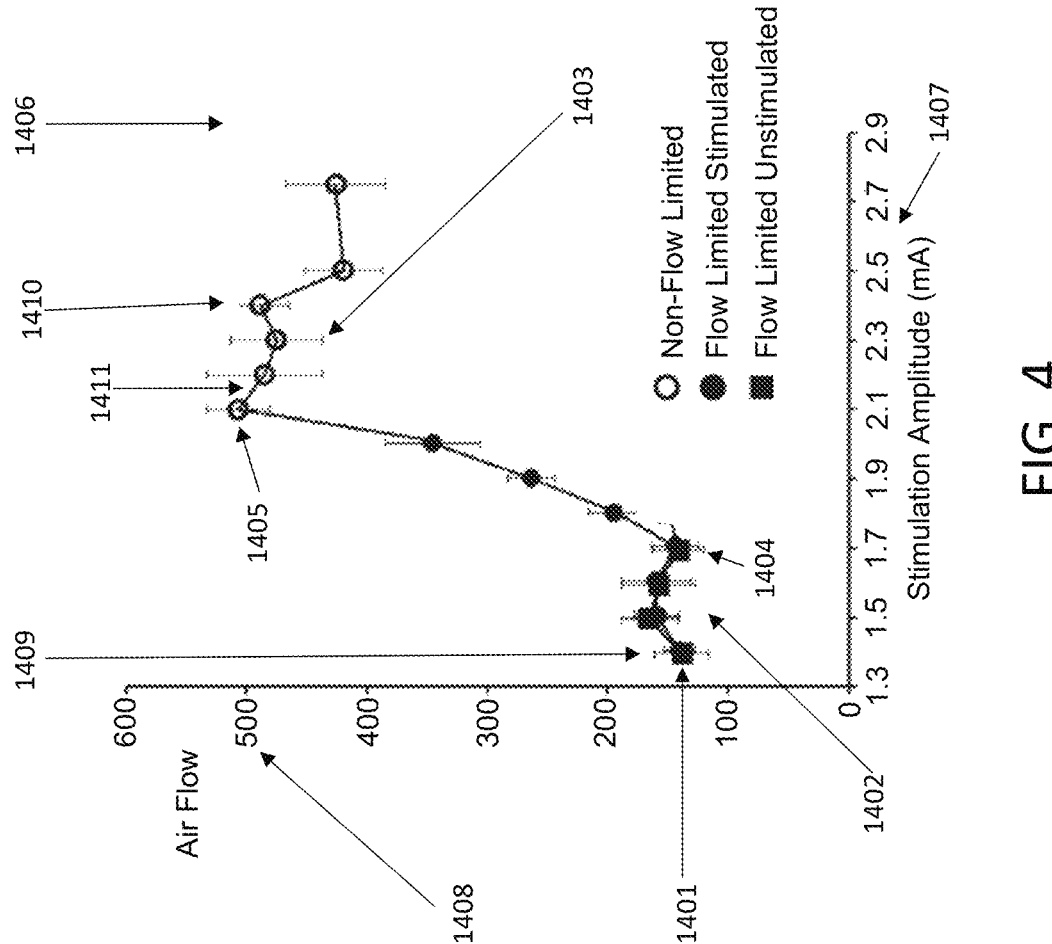
FIG. 4 is an XY graphical representation of the breathing airflow of an OSA patient on the Y axis in response to the hypoglossal nerve stimulation intensity on the X axis.

The stimulation intensity set by the titration procedure is an important parameter that can easily affect efficacy if too low, or discomfort, arousal, or cause pain if too high. Hence, the titration method leading to the therapy level of stimulation is an important step prior to using the device. FIG. 4 shows a graph of an OSA patient's air flow 1408 on the Y axis vs. stimulation amplitude 1407 on the X axis during sleep. Air flow is at a low plateau 1402 up to the flow capture threshold 1404 when stimulation amplitude is insufficient to trigger meaningful genioglossus muscle contractions. Air flow is at a high plateau 1403 starting from the peak flow threshold 1405 when stimulation amplitude has fully moved the tongue out of the airway. The arousal threshold 1406 in FIG. 4 is the level of stimulation amplitude that awakens the OSA patient.

In FIG. 4, the twitch threshold 1401 of the tongue is an observable threshold while the patient is awake. So, the first step in the titration procedure of this device to increase the amplitude by pushing the button 1301 in FIG. 3A on the wearable in "Intensity Setup" mode in Table 1 until these muscle twitches are observed. Each push of the button increases the amplitude by 14.4%. Pushing the button repeatedly generates a series of fixed percentage increases in stimulation amplitude. Once the initial muscle-twitch level of the tongue is observed, the next step is to further increase the amplitude until the expected air flow reaches the higher plateau 1403 in FIG. 4, but is still less than the arousal threshold 1406. The titration algorithm is to press the button 4 times to achieve a $(1.144)^4 = 1.712\times$ increase in amplitude. For the example shown in FIG. 4, this will increase the stimulation amplitude from the 1.4 volts of the twitch threshold 1401 to 2.4 volts 1410 within the high plateau 1403 but far from the arousal threshold 2.9 volts 1406 in FIG. 4. Even though less than the arousal threshold, this titrated amplitude of 2.4 volts 1410 may still be objectionable or discomforting to the patient. So, the protocol allows for the physician to back off the amplitude by one level (−14.4%), to 2.1 volts 1411 in FIG. 4, which is still within the high plateau 1403.

Regarding the X axis 1407 in FIG. 4, this scale will change if the stimulating electrode 1702 in FIG. 7D is further from the nerve (stimulation thresholds will increase), and the opposite is true if the electrode is closer to the nerve. However, this titration procedure uses the muscle-twitch level threshold 1401 as a reference point and scales from it, so a robust outcome is expected from patient to patient and over a variety of electrode placements. Depending on these variations, the twitch threshold may be between 0.1 and 10 volts, and the final titrated therapy level may be between 0.2 and 24 volts.

Bench Test Results

Figure 8B:
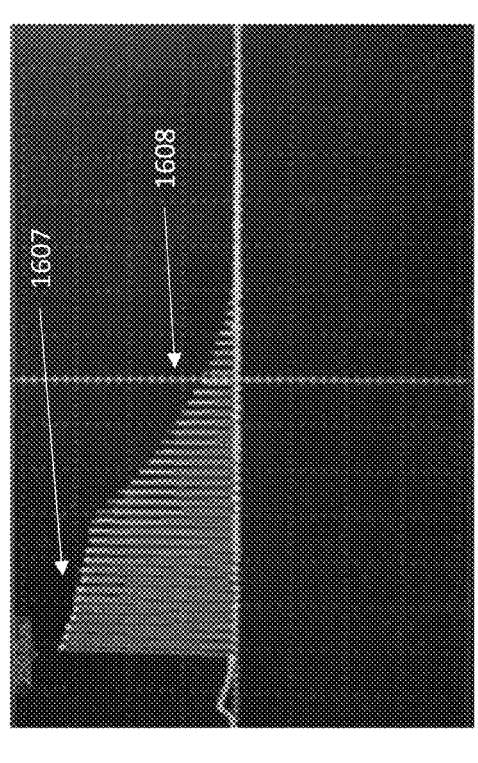
FIG. 8B shows a corresponding oscilloscope trace of the voltage across the injectable's electrodes with a time-scale.
Figure 8C:
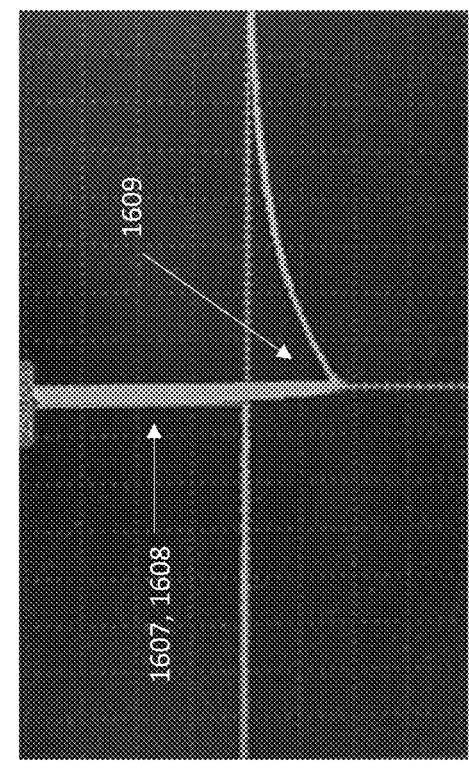
FIG. 8C shows a corresponding oscilloscope trace of the voltage across the injectable's electrodes with a different time-scale.
Figure 8A:
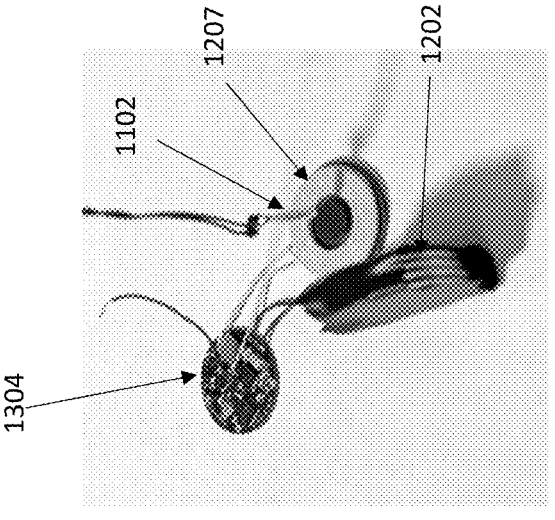
FIG. 8A shows an embodiment of the injectable and wearable electronics with one type of field-generating coil.

FIG. 8A shows an embodiment of the wearable 1101 of FIGS. 1A and 3A to 3C, without the parts integrated into a tight package. Circuit board 1304, pack of 2016 size coin batteries 1202 and field-generating coil 1207 are built, connected, and functioning as intended in FIG. 8A. An injectable 1102 circuit is built as shown in FIG. 5C, and is placed above the wearable coil by 1 centimeter. The waveform periods of FIG. 6B are readily observed on the oscilloscope trace in FIGS. 8B and 8C. The waveform period where the voltage is clipped by the Zener is shown in period 1607 of FIG. 8B. The waveform period of following the natural exponential decay of the wearable output is shown in period 1608 of FIG. 8B. And, the charge balancing period is shown in period 1609 of FIG. 8C. The three periods correspond to and resemble those in FIG. 6B. The wearable coil 1207 in FIG. 8A is 2 centimeters in diameter with two layers of Litz wire windings on a ferrite disk.

Figures 9A, 9B:
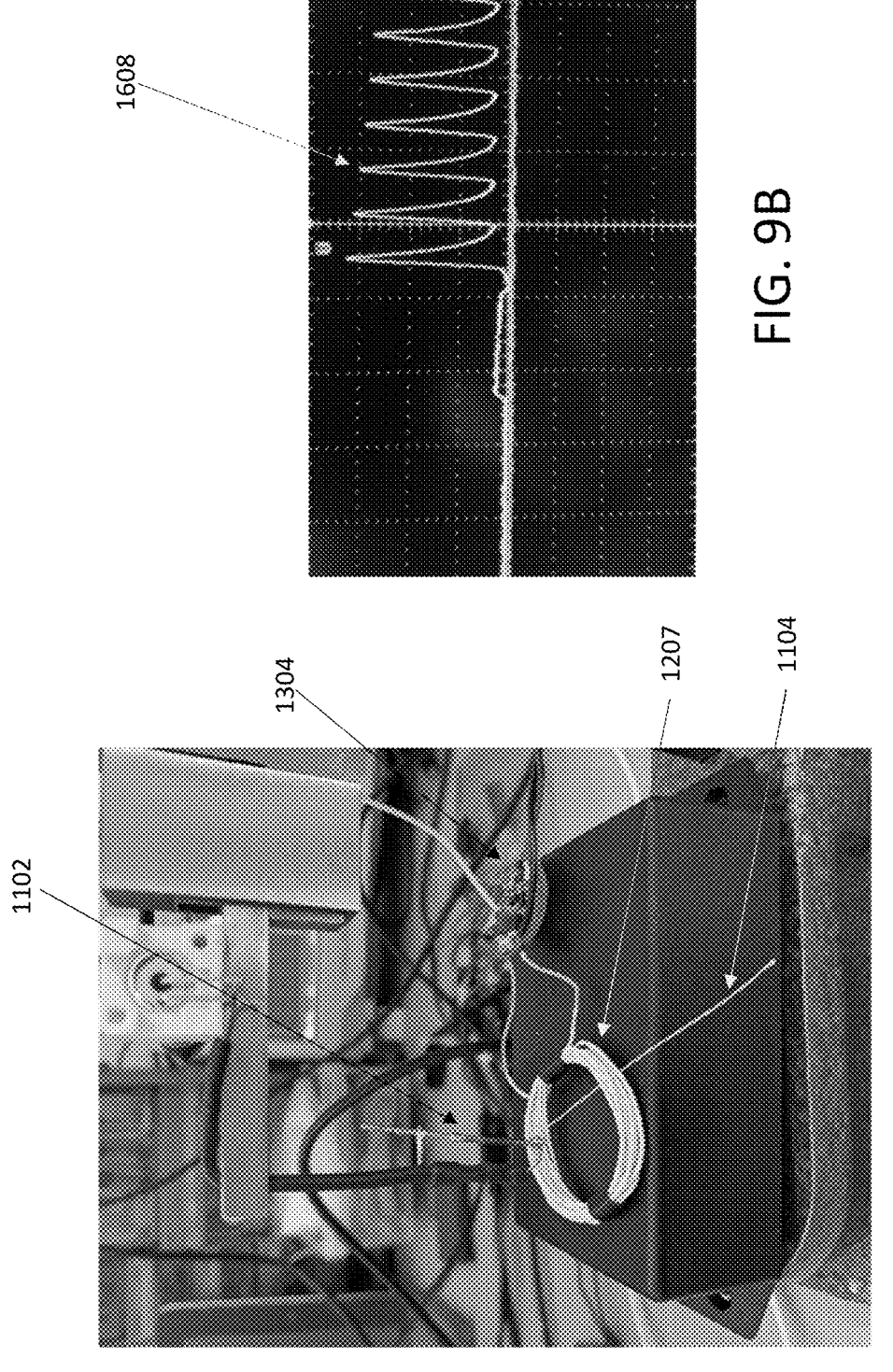
FIG. 9A shows an embodiment of the injectable and wearable electronics with another type of field-generating coil.
FIG. 9B shows a corresponding oscilloscope trace of the voltage across the injectable's electrodes.

FIG. 9A shows a similar apparatus as FIG. 8, but with a larger wearable coil 1207 that has a diameter of 3.5 centimeters, 9 turns, and wound from 24-gauge Litz wire. The spacing between the injectable 1102 and the wearable coil 1207 is 2.5 centimeters, which is the maximum distance expected for hypoglossal nerve stimulation in a population of OSA patients. The oscilloscope trace 1608 in FIG. 9B indicates an amplitude response of over 10 volts, sufficient to fully stimulate the hypoglossal nerve even at this maximum separation distance.

Introducer Description

Figure 10B:
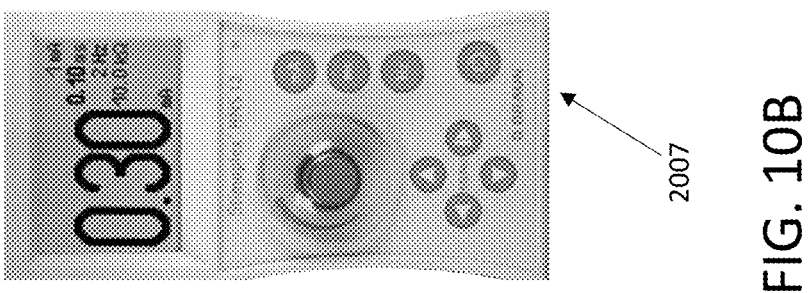
FIG. 10B shows one embodiment of the corresponding needle-tip stimulator.
Figure 10A:
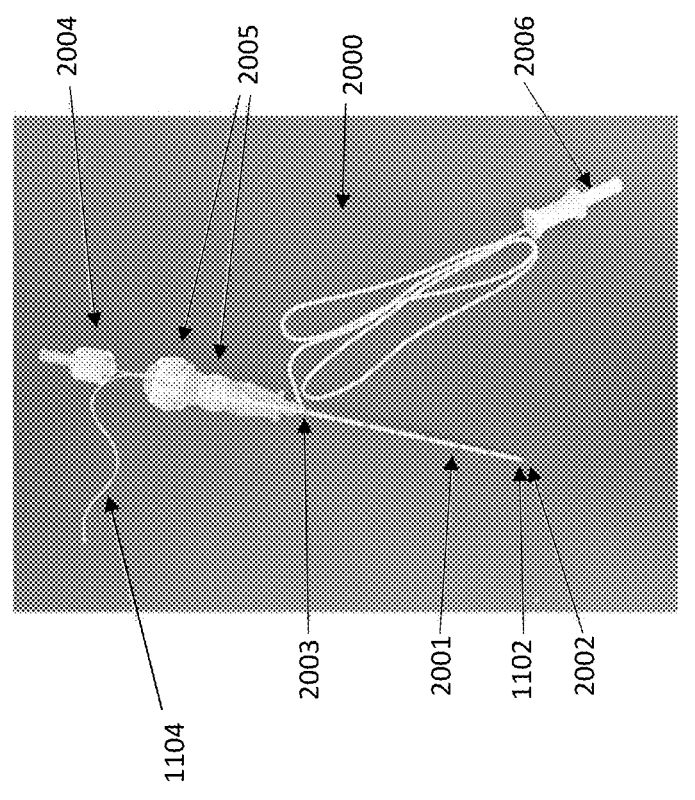
FIG. 10A shows an introducer needle with a connector to a needle-tip stimulator and a sliding plunger rod containing an elongate injectable having a tether.

The injectable 1102 is intended to be pre-loaded by the manufacturer in the introducer needle 2001 as shown in FIG. 10A. The needle tip 2002 has stimulation capability and connects to the B Braun HNS12 hand-held neural stimulator 2007 FIG. 10B. This stimulator is designed to stimulate nerves for nerve-block injections during anaesthesia. The stimulation capability will be used to validate that the tip of the needle is in fact at the hypoglossal nerve before deploying the injectable at that location. The connection between the stimulator 2007 and the needle 2001 is made by wire 2006 in FIG. 10A soldered or crimped 2003 to the needle of the introducer near the hub. The introducer needle is insulated with a coating of Parylene of thickness 1 to 50 microns, or other insulation, except the region 1 millimeter from the tip 2002 or other distance from the tip, in order to concentrate the stimulation at the tip. The tip 2002 is blunt and has a short 30-degree bevel to allow for tunnelling through tissue during injection but not harming a nerve or vessel if either is contacted unintentionally.

In FIG. 10A, the injectable 1102 is pre-loaded at the tip 2002 of the needle, and the tether 1104 is routed through the needle. Both the tether 1104 and plunger 2004 are the routed through the locking iris valve 2005, which is tightened at the factory to hold the components in place until deployment of the injectable. The locking iris valve 2005 is opened by twisting the two knobs away from each other. This mechanism allows the physician performing the injection to ultrasound-guide the needle to the hypoglossal nerve, and then have an assistant loosen the locking iris valve 2005 just prior to deployment of the injectable 1102.

In FIG. 10A, the introducer needle 2001, may be Bard part number C1813B (BARD MEDICAL, New Providence, NJ), and then coated with (insulating) Parylene except for the tip to convert this needle into a stimulating needle. The wire with the stimulator connector 2006 available from anaesthesia needle B Braun part number 33644. The locking iris valve 2005 may be Merit Medical part number FLO30 (MERIT MEDICAL SYSTEMS, South Jordan, UT). The plunger 2004 is a custom 22-gauge rod.

Injection Procedure and Wearable Placement Protocol

Below is an example of the manufacturer's instructions for injecting the device and preparing the patient for neuromodulation therapy for OSA.

1. The assistant or physician unpacks the pre-loaded introducer 2000 in FIG. 10A, wraps a sterile shroud around the ultrasound probe and cover it with sterile gel. Then, place a skin electrode near the collarbone of the patient and electrically connect it to the handheld B Braun HNS 12 stimulator 2007 in FIG. 10B. The stimulator is also connected to the lead wire 2006 of the introducer needle 2000 as shown in FIG. 10A. Configure the handheld stimulator to generate 1 millisecond pulses at a frequency of 1 Hz. Set the initial current to 0.0 milliamps.

Figures 12A, 12B:
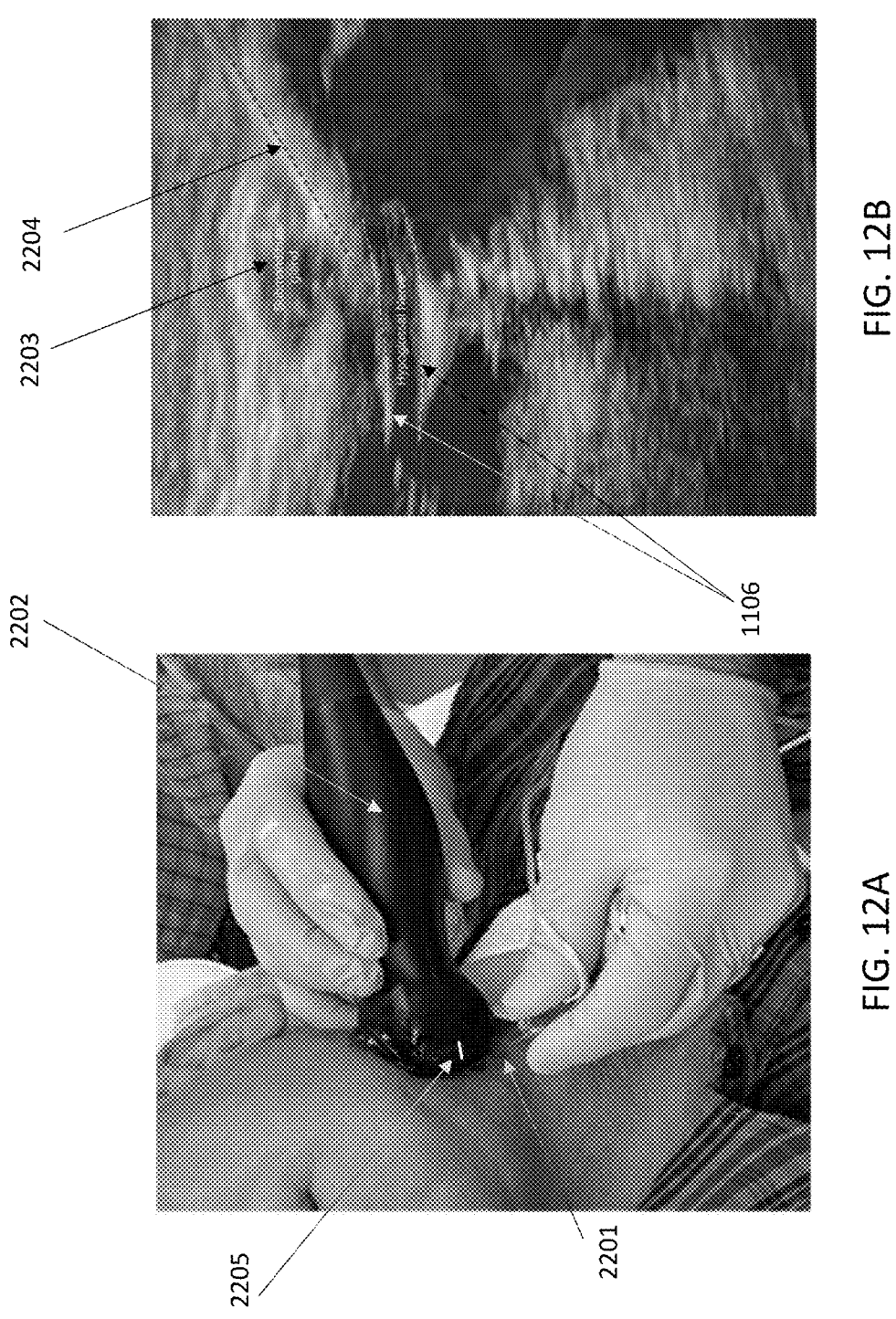
FIG. 12A shows the ultrasound imaging probe and the entry point of the needle to reach the hypoglossal nerve along an injection path for the elongate injectable device.
FIG. 12B is the corresponding ultrasound image of the needle reaching the hypoglossal nerve marked up to highlight this and other key features.

2. The physician places the ultrasound probe, covered with gel, on one side of the neck underneath and parallel to the jawbone. The physician moves the ultrasound probe until the submandibular gland and parallel tracks of the hypoglossal nerve 1106 are visible as indicated in FIG. 12B. If the ultrasound probe indicates the upper track of the hypoglossal nerve is deeper than 2.5 cm, then the procedure is stopped and the subject is disqualified.

3. The physician then visualizes a linear path 2204 to the skin surface from the hypoglossal nerve that safely skirts the submandibular gland 2203 in FIG. 12B. During visualization, the physician identifies an entry point of the needle, and mark this location on the skin. The physician ensures the mark is carefully aligned with the center fiducial 2205 on the side of the probe in FIG. 12A.

4. The assistant or the physician wipes clean the needle entry point and inject the local anesthetic, Lidocaine.

5. The physician allows a few minutes for the anesthetic to take effect, then using a surgical needle, makes a small puncture at the marked entry point.

6. The assistant covers the ultrasound probe with sterile gel. The physician will then, with one hand, return the ultrasound probe to the side of the neck underneath and parallel to the jawbone. Ensure the mark is carefully aligned with the center fiducial 2205 on the side of the probe in FIG. 12A. The physician moves the probe until the submandibular gland is again visible with the parallel tracks of the hypoglossal nerve 1106 just beyond it in FIG. 12B.

7. Then, with the other hand, the physician inserts the introducer needle 2000 in FIG. 10A anteriorly from the under-chin area and guide it along the edge of the submandibular gland toward the hypoglossal nerve. The physician (1) avoids going through the submandibular gland, (2) keeps the needle on a linear trajectory to the nerve target, and (3) maintains view of the needle, submandibular gland, and the hypoglossal nerve at all times. The physician may reposition, redirect, and/or reinsert the introducer as needed to accomplish these. See FIGS. 12A and 12B.

8. Once the tip of the introducer tip 2002 in FIG. 10A is within 1-2 millimeters of the hypoglossal nerve, the assistant will increase the current output of the handheld stimulator 2007 in FIG. 10B until tongue movements are observed. The assistant increases the current until tongue displacements appear to saturate by when tongue displacement stops increasing. If saturation is not seen with 2 milliamps of stimulation with 1 millisecond pulses at a rate of one per second, the physician moves the introducer tip closer to the nerve, if possible.

9. The physician places the injectable by having the assistant loosen the locking iris 2005 in FIG. 10A of the introducer in—while holding the plunger 2004 fixed in space and pulling the introducer needle 2000 out simultaneously. The physician and assistant ensure that the downstream stimulating end of the injectable 1102 in FIG. 10A remains within 1-2 mm of the hypoglossal nerve on the ultrasound display. The introducer should now be completely outside the subject and the injectable's stimulating electrode should be within 1-2 mm of the hypoglossal nerve. With the physician's or assistant's finger on the tether entry point, the injection site is gently cleaned, and the excess tether 1104 in FIG. 10A is coiled and taped to the subject's skin away from the injection site. The physician and assistant are careful to not pull the injectable away from the nerve. The physician or assistant places a bandage, such as Tegaderm 3582 from 3M (Minnesota) such that the pad gently covers the injection point. Note that for permanent placement of the injectable, the tether will not be present or may be made from a synthetic absorbable material.

10. This next step is performed at some time after the injection is complete, possibly depending on whether the placement is temporary for an overnight test, or permanent. The physician or assistant remove the wearable's adhesive covering and centers the wearable on the injectable's location, and is not centered on the needle entry point. The wearable is attached to the subject's skin, overlapping with the bandage if necessary and if still present.

11. A physician, possibly different from the physician who placed the injectable, sets the wearable to Intensity Setup Mode, following Table 1. In this mode, stimulation will alternate on and off at 1 second intervals at the lowest level. The physician increases intensity one level at a time by pressing the button once quickly for each level, as designated in Table 1. When the physician observes the twitching-threshold stimulation level 1409 in FIG. 4 of the tongue, the physician increases the stimulation by pushing the wearable's button quickly 4 times to increase the amplitude to level 1410 in FIG. 4. If this level of stimulation is uncomfortable for the patient, the physician may decrease the stimulation by one level, to amplitude level 1411 in FIG. 4 by pressing the button twice quickly as denoted in Table 1. Then, the physician holds the button for 1-2 seconds to fix this stimulation level in the wearable's memory inside the microprocessor 1200 in FIG. 2C, as denoted in Table 1.

If the device cannot reach a higher level of intensity when the button is pushed, then the LED will not provide its blinking feedback. If this happens during the titration process, then proper titration is not achievable. This may be due to excessive distance between the injectable and nerve or excessive distance between the injectable and wearable. The physician decides if a second injection attempt is warranted. If so, the injectable is removed via the tether, if present; the injectable and all introducer parts are discarded, the skin around the injection site is cleaned, and the above steps are repeated with a new introducer and new injectable.

The Frequency Setup Mode in Table 1 can be used if the patient is still not comfortable with the stimulation, adjusting to a higher or lower frequency. The titration procedure in Step 11 must be repeated after changing the frequency.

Once the wearable parameters are fixed in Step 11, the patient may place the wearable prior to sleep, and the patient may remove the wearable after sleep. The patient may also recharge or replace the batteries 1305 in FIG. 3C.

12. The physician or the patient fits the breathing sensor 2306 on the chest or abdomen, possibly underneath the breathing belt normally used in sleep studies, as illustrated in FIG. 13C, 13D, or 13E. The physician or patient routes and connects the breathing-sensor wire under the shirt or other upper garment, through the collar and to the wearable as shown in FIG. 1A. On the first use, the physician will ensure the breathing sensor is working by observing the wearable's LED being on during the subject's inhalation.

Animal Demonstration in Rat Sciatic Nerve

Figure 11B:
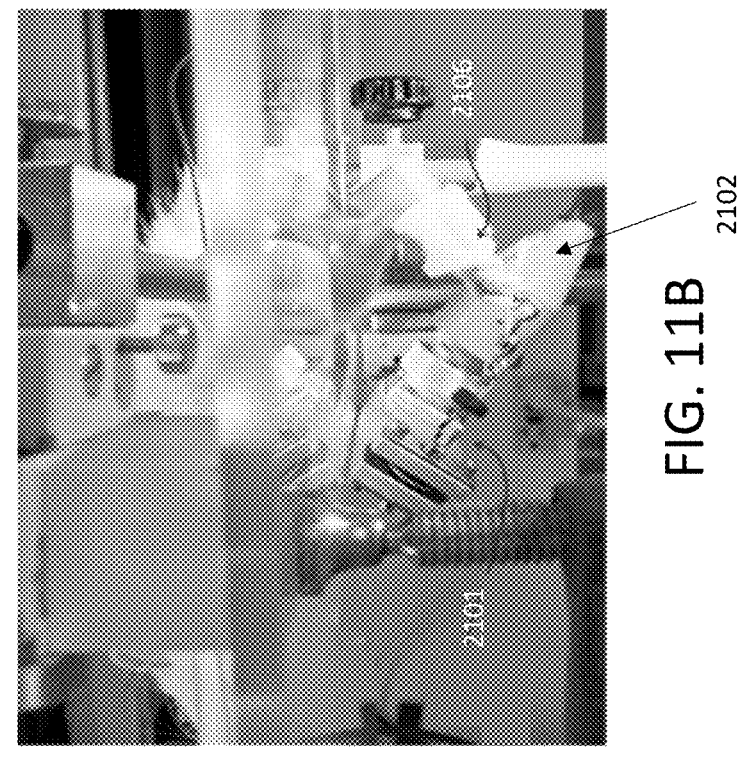
FIG. 11B shows another portion of the apparatus for proving the concept of the wireless stimulator and elongate injectable in an animal.
Figure 11A:
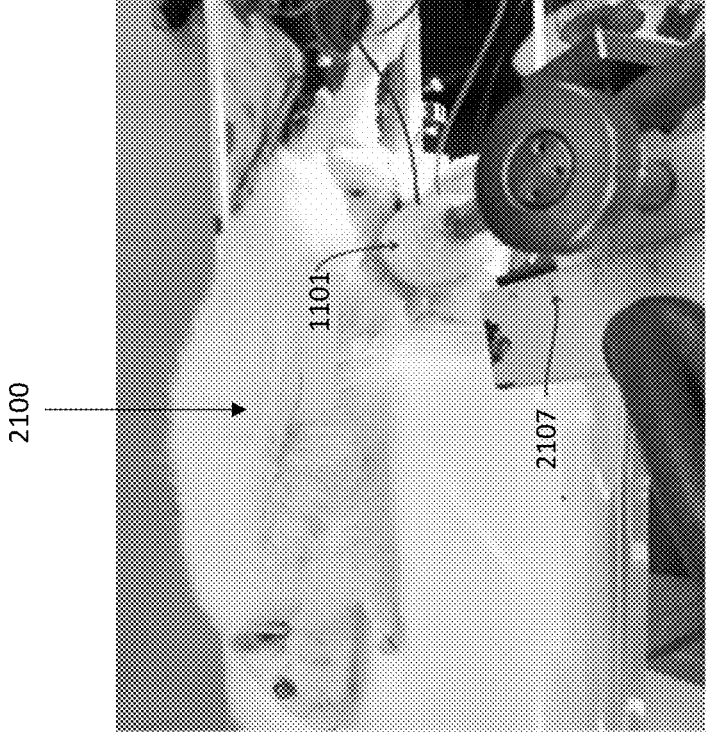
FIG. 11A shows one portion of the apparatus for proving the concept of the wireless stimulator and elongate injectable in an animal.

The full function of the wearable and injectable devices was demonstrated in a rat's sciatic nerve, using the apparatus in FIGS. 11A and 11B. The sciatic nerve of a rat is approximately 2 millimeter in diameter, the same as the hypoglossal nerve in a human. The injectable was placed at the sciatic nerve of rat 2100 by surgery, and then the wound was closed and sutured. The wearable 1101 was placed on a calibrated movable stage 2107. The corresponding hind leg paw of the rat was affixed to a pedal 2102 which was physically connected to a force transducer 2101. This apparatus of FIGS. 11A and 11B allowed for measurements of the hind leg force as a function of distance of the wearable from the nerve.

Figure 11C:
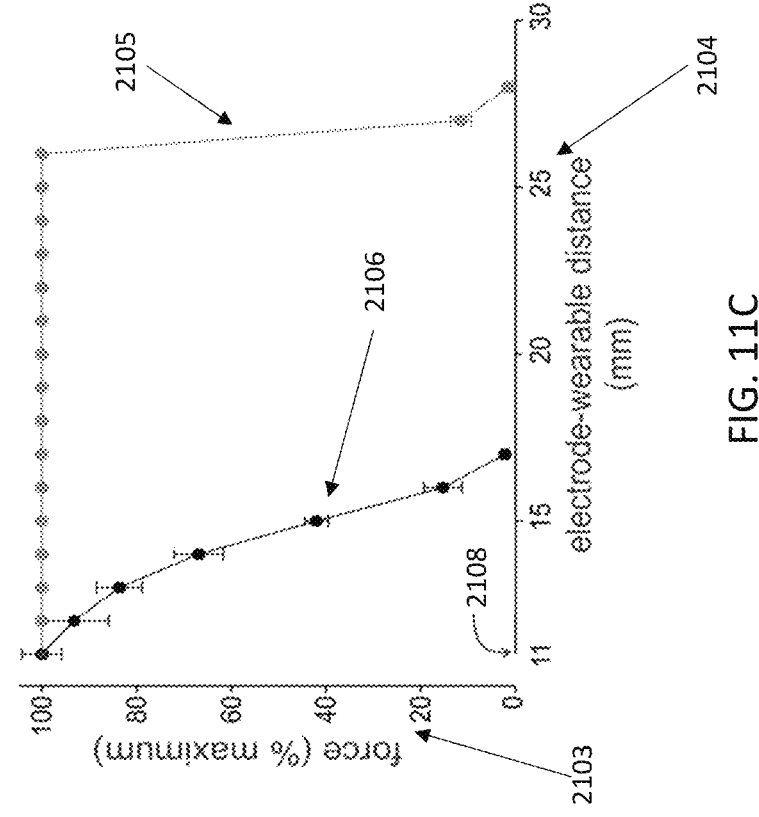
FIG. 11C is a corresponding XY graphical representation of the measurements of animal muscle forces in response to the neurostimulation vs. the distance of the wearable from the nerve, for two different field-generating coils.

The results of this study are shown in FIG. 11C. The hind leg force 2103 measured by the transducer 2101 is displayed on the Y axis. The distance of the wearable 1101 from the sciatic nerve is shown on the X axis, wherein the skin surface was 11 mm from the nerve indicated by point 2108. The force was measured for two different coils 1207 in FIG. 2B shown by graph 2106 in FIG. 11C and second coil 1207 in FIG. 9A shown by graph 2105 in FIG. 11C. The hind leg force exceeded the capacity of the force transducer, making the graph 2105 flat before decreasing with distance. The data indicates that the distance capability of the wearable with the smaller coil is 15 millimeters away from the nerve and with the larger coil 27 millimeters away from the nerve. The hypoglossal nerve in a human is expected to me a maximum of 25 millimeters from the wearable in a majority population of OSA patients.

Human Demonstration of Ultrasound-Guided Injection Path

In two human subjects, an otolaryngologist safely ultrasound-guided a nerve-block needle along the expected injection path of the introducer shown in FIG. 10A from the skin surface, avoiding the submandibular gland, and reaching proximity to the hypoglossal nerve. The ultrasound system 2202 in FIG. 12A was manufactured by Butterfly iQ (BUTTERFLY NETWORK, Guilford, CT) with an Apple iPad display showing the image as in FIG. 12B. The stimulation needle 2201 in FIG. 12A was inserted under the chin at a roughly 30-degree angle to the skin towards the hypoglossal nerve 1106, and carefully avoiding the submandibular gland 2203. This needle was guided by the physician holding an ultrasound probe 2202 such that the length of the needle 2204 was in the planar view of the ultrasound display in FIG. 12B. The location of the needle tip at the hypoglossal nerve was verified by activating the needle tip with the stimulator in FIG. 10B. Tongue protrusions were observed in both human subjects, which is the expected response to hypoglossal nerve stimulation for OSA. No significant discomfort was reported and no vessels or other sensitive structures were observed in the region imaged in FIG. 12B or its surroundings, even when the Doppler feature of the ultrasound system was highlighting blood flow.

Breathing Sensor

The breathing sensor is a piezoelectric disk that flexes against a pivot, generating a positive voltage when the patient is inhaling and a negative or zero voltage otherwise. The major components of the breathing sensor are as follows in FIG. 13A: a piezoelectric disk 2301 often found in electronic buzzers. The piezoelectric disk has a diameter of 35 millimeters and is available from Murata part number 7BB-35-3L0 or other piezoelectric disk; a support disk 2302 made of brass or other suitable material to provide a parallel plate for the pivoting motion; a pivot 2303 which is a clear rubber dome from 3M (St. Paul, MN), Electronics part number B073W1B3G1 or other pivot affixed to the center of the support disk 2302; a felt pouch shown in FIG. 13B to house the stack up of the brass disk 2302, pivot 2303, and piezoelectric disk 2301; a hook-and-loop strip 2304 at the opening of the pouch for insertion of the stack up. Without limitation, the pouch could be made of another suitable material such as cloth that may be a moisture barrier or lined with a moisture barrier layer or coating. The output wire from the piezoelectric disk is knotted with the knot below the hook-and-loop seal 2304 for strain-relief, or may be crimped to the support disk 2302. Another strain relief could also be used to affix the wire to the pouch such as a crimp attached to the pouch, a knot hole in the pouch threaded by the wire, a sewn-on attachment or other suitable means.

Figures 13A, 13B:
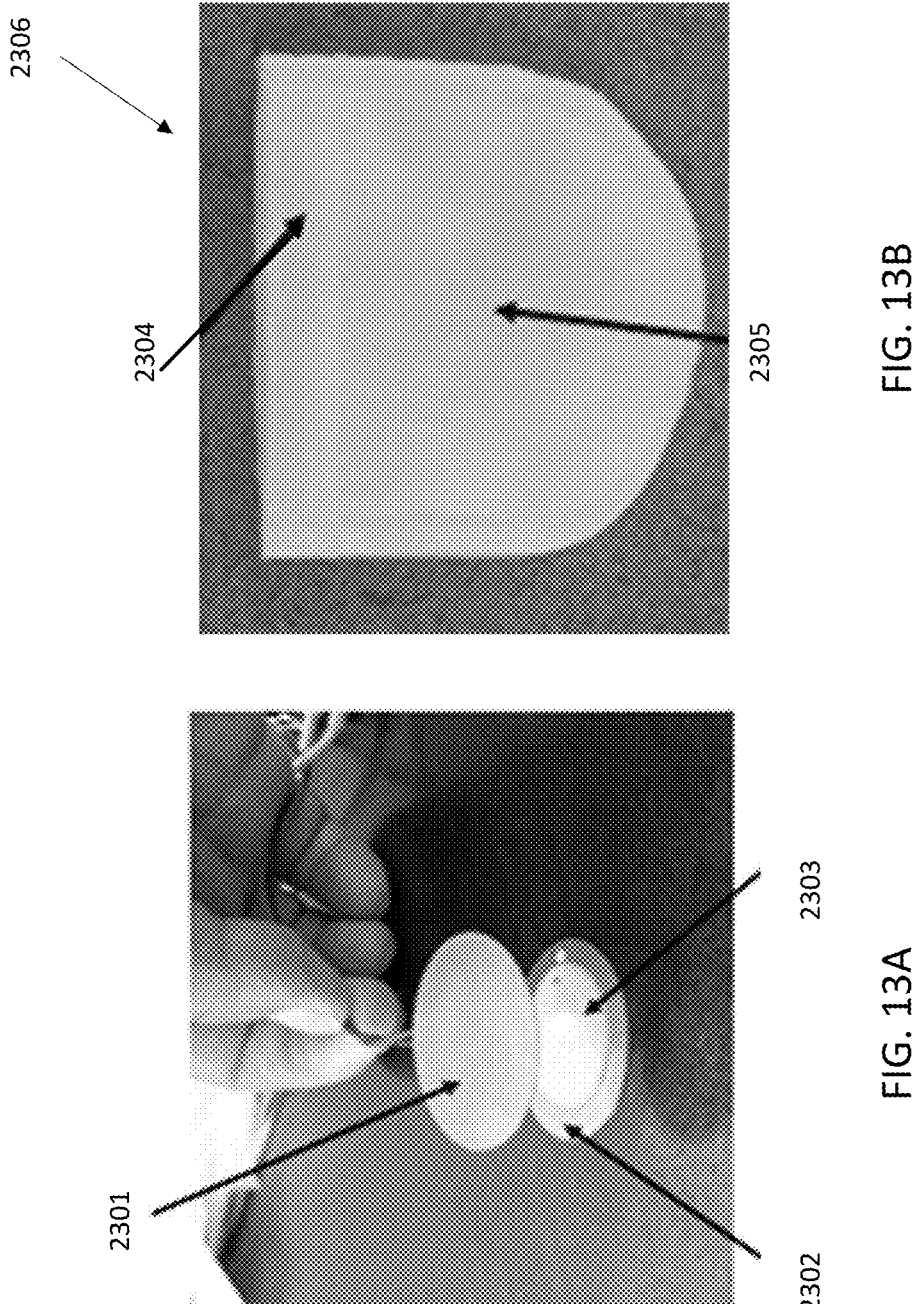
FIG. 13A shows the stack of components comprising the breathing-motion sensor.
FIG. 13B shows the corresponding container or pouch for the components of the breathing-motion sensor.
Figures 13C, 13D, 13E:
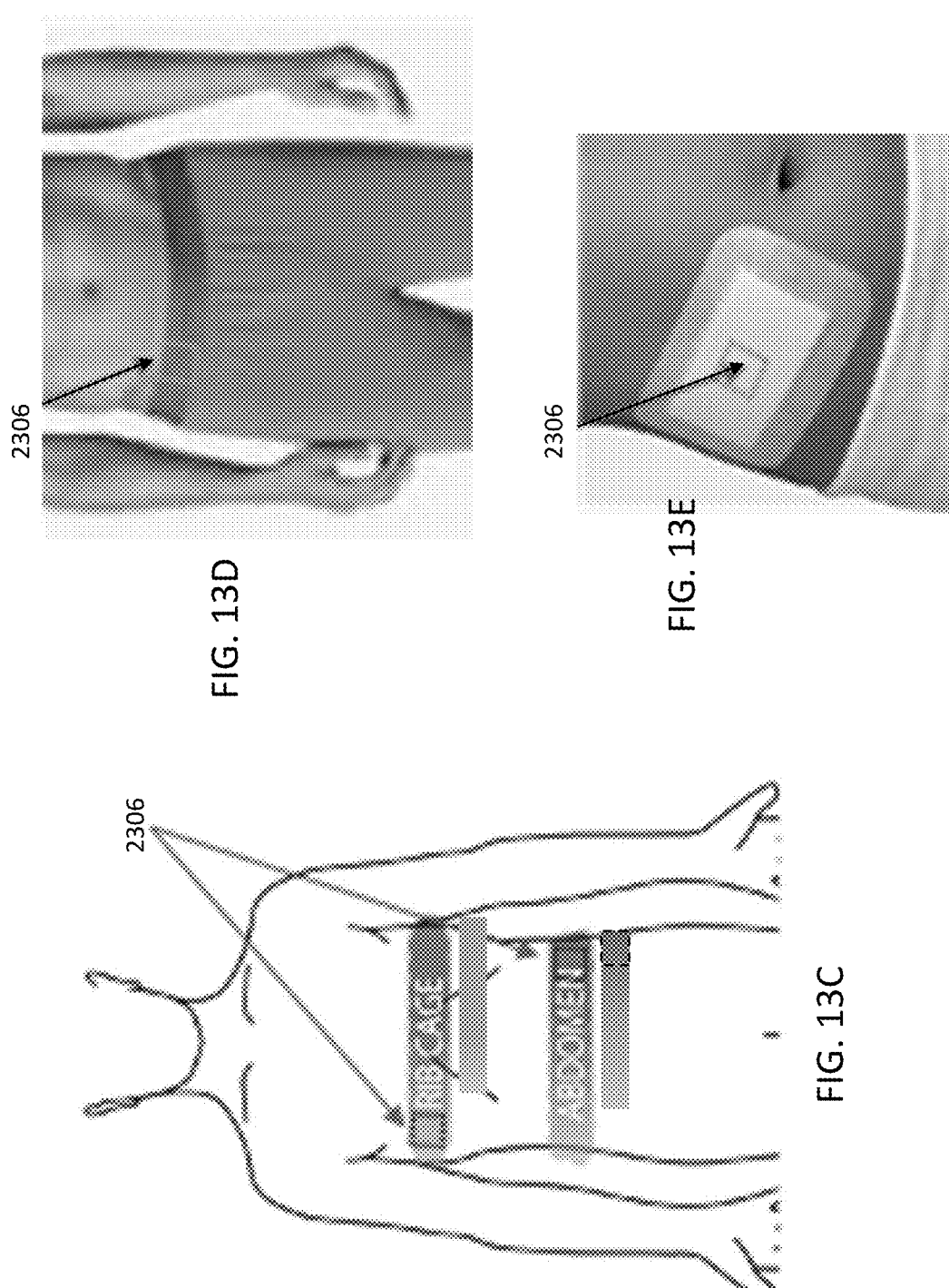
FIG. 13C shows two methods and locations for affixing the breathing-motion sensor to the body.
FIG. 13D shows another method and location for affixing the breathing-motion sensor to the body.
FIG. 13E shows yet another method and location for affixing the breathing-motion sensor to the body.

FIG. 13A shows a piezoelectric disk 2301 intended for use as a buzzer. Without limitation, this part of the sensor is 35 mm in diameter and contains a piezoelectric ceramic film on one side. Wires are connected the ceramic and to the brass substrate. A capacitance of 30 nano-Farads exists between the ceramic and the substrate. In its intended use, a voltage is applied to the wires, causing the disk to vibrate, or buzz audibly, at a fixed frequency. In this application for this invention, this disk generates a voltage when the substrate is flexed slightly. Without limitation, an example of this part is 7BB-35-3L0 manufactured by Murata (Kyoto, Japan).

This breathing sensor generates a voltage when the piezoelectric disk is flexed as the chest or abdomen expands during inhalation, and with the configuration of FIG. 13A, the voltage is positive when the piezoelectric disk 2301 is flexed toward the support disk 2302 and the support disk is facing the body. The flexing motion causes charge to build up across a ceramic film on the piezoelectric disk, generating a voltage. Even if the flexing force remains, the voltage will decline over time as the charge is dissipated by a resistance. The time constant of this decline in voltage is RC where R is the total resistance in parallel with the sensor output and C is the native capacitance of the piezoelectric disk. Hence, the time constant of this voltage decline may be designed-in by a prescribed load resistance or series resistor inserted between the sensor output and the load.

The sensor's piezoelectric disk will flex with the patient's breathing motion if a strap is routed and tensioned across the back of the sensor and either attached to the skin on either side or routed fully around the body. This strap-mounting may locate the sensor anywhere between and including the upper chest, lower chest, the stomach area, the abdomen area, and the waistline. Preferentially, the sensor is located on the chest for patients expand the chest when they inhale and close to the waist for patients that expand the stomach when they inhale. In addition, the strap may be a breathing belt as depicted in FIG. 13C with the sensor at location 2306, or may be the elastic or cloth waistline portion of a garment or undergarment as depicted in FIG. 13D with the sensor at location 2306, or may be taped or bandaged from behind to the skin on either side as depicted in FIG. 13E with adhesive tape or an adhesive bandage with the sensor at location 2306.

Figures 14A, 14B:
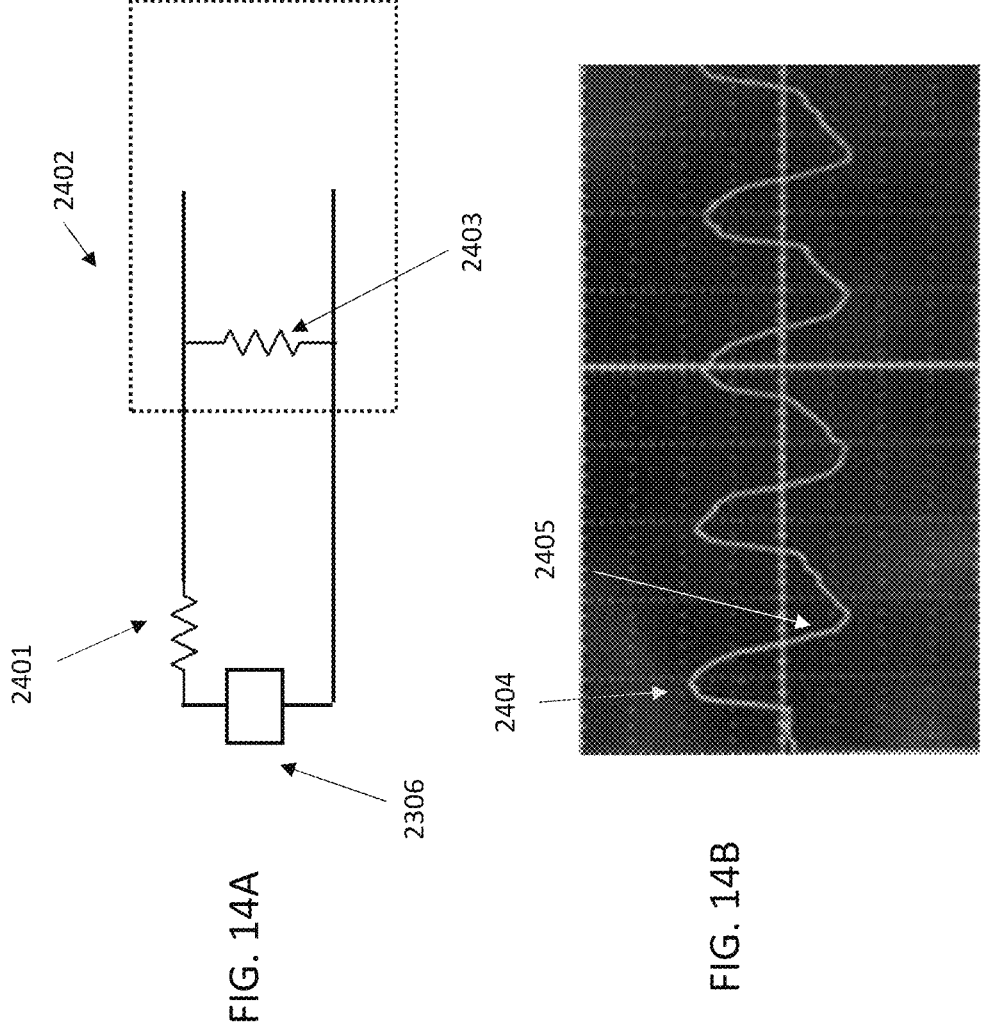
FIG. 14A is a schematic representation of the circuit used to interface the breathing-motion sensor to the analog-to-digital converter input of the wearable field generator.
FIG. 14B is an oscilloscope trace of the breathing motion sensor output in response to human breathing.

In FIG. 14A, the load resistance is the input impedance of the sensor's 2306 downstream analog-to-digital converter or preamplifier 2403 plus a series resistance 2401 that is added to design-in a desired time constant. In numerous experiments by the inventor, the desired time constant for a sensor that can accurately detect the inhalation phase of breathing is around 0.3 seconds for this model of piezoelectric disk 2301 in FIG. 13A. This time constant results in the sensor output being mostly of positive voltage when the patient is inhaling or attempting to inhale, and a mostly negative voltage when the patient is not inhaling. Because the native capacitance of piezoelectric disk 2301 is 30 nano-Farads, a load resistance of 10 MOhm will generate this desired time constant. As indicated in FIG. 14A, this load resistance can be achieved by adding a series resistor 2401 with a resistance of 10 MOhm minus the input impedance of the A/D converter input on the microprocessor 1200 of the wearable in FIG. 2C or of the wireless transmitter replacing the wired connection. Without limitation, the selected time constant of the sensor for other patients' breathing patterns and rates could be 0.1, 0.2, 0.4, 0.5 or 0.6 seconds or any value therebetween.

FIG. 14B shows an oscilloscope trace of the voltage from the sensor when mounted as indicated in FIG. 13D (waistline). The input impedance of the oscilloscope is 1 MOhm, so the series resistor 2401 in FIG. 14A was selected to be 9 MOhm for this bench test. In the trace of FIG. 14B, inhaling is occurring almost exclusively when the voltage output is positive 2404 and the voltage output is almost exclusively negative 2405 otherwise. The sharp rising edge of the voltage 2404 crossing zero volts just prior to the inhalation phase serves as a strong and reliable signal to turn on a neural stimulator of the hypoglossal nerve to move the tongue out of the airway and allow a patient with OSA to inhale without blockage.

Similar signals to that of FIG. 14B with positive voltage during inhaling and attempting to inhale and negative voltage during exhale were observed in all sleeping positions, including lying on either side, lying on back, and even lying front down with the weight of the body on the sensor against the mattress.

Without limitation, the piezoelectric disk 2301 of FIG. 13A could be of a different size, shape, or capacitance and still be designed into a breath-motion sensor by someone skilled in the art. Without limitation, the desired time constant may be restored for a different native capacitance and/or load resistance by changing the series resistor.

Improved TENS Device

Figure 15:
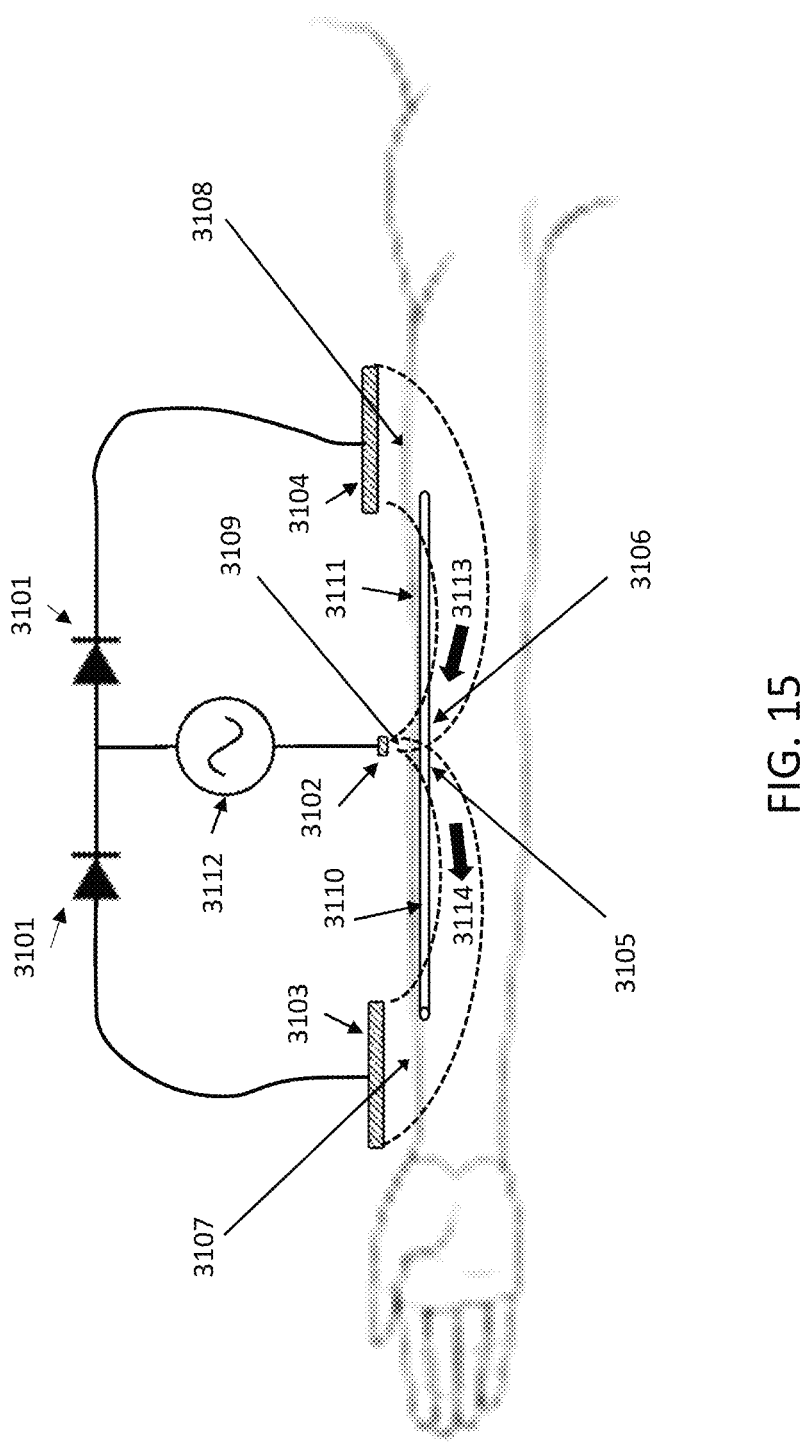
FIG. 15 is an embodiment of a novel and improved transcutaneous electrical nerve stimulation (TENS) system for peripheral nerves and muscles.

FIG. 15 shows the invention applied to transcutaneous stimulation at a location on the human arm. Without limitation, the configuration of FIG. 15 could be placed at any location on the body where nerve or muscle stimulation is desired. In this case, a nerve 3110 is the target for the stimulation. Three electrodes 3102, 3103, and 3104 are mounted on the skin 3111. Electrode 3102 is the stimulating electrode, and electrodes 3103 and 3104 receive oppositely rectified components of the alternating current, as will be described below. The rectifying circuit or component may be two diodes 3101.

Without limitation, stimulating electrode 3102 could be split into an array of smaller electrodes, some of which provide positive components of the AC waveform and others providing negative components. These variants of the invention are considered to be essentially the same art as described here, as the aggregate effect is the same.

An alternating current (AC) voltage source 3112 has one terminal connected to the stimulating electrode 3102, and the other terminal is connected to the cathode of one diode 3101 and to the anode of another diode 3101. Diodes 3101 ensure a different path through the body for the positive pulses vs. the negative pulses that comprise the alternating current or voltage source 3112. The path of the positive pulses 3113 can be considered the path of anodic current and the path of the negative pulses 3114 can be considered the path of cathodic current. As these two paths merge at electrode 3102, this merged region sees both positive and negative pulses, or full AC stimulation.

In order to stimulate a nerve 3110, a combination of both intensity or amplitude and current density is required. A nerve can be stimulated by either cathodic or anodic current, but generally twice the amplitude is required for anodic current vs. cathodic current. In FIG. 15 the cathodic current density is highest location 3105, and this location is the target for stimulation. Location 3106 is the location of highest anodic current density, and this location can provide a desired cancellation of the cathodic stimulation at 3105 so that brain-bound action potentials are not created at sensory nerve fibers that may coexist with motor fibers in nerve 3110. Alternatively, the cathodic and anodic currents could be reversed by physically reversing the return electrodes thereby using the stronger cathodic current to relieve pain signals toward the brain while the anodic current prevents or minimizes excitation of muscular fascicles downstream of the cathodic excitation.

In FIG. 15, locations 3107, 3108, and 3109 under each electrode are most susceptible to the side effect of electric shock feeling as current is passing through superficial nerve endings that are easily excited. In the prior art TENS devices, these locations would be the sources of shock sensation. However, in this invention configuration of FIG. 15, none of these locations 3107, 3108, and 3109 need to cause electric shock sensation.

At the location of the stimulating electrode 3109, these nerve endings near the skin experience alternating current. The Underwriters Laboratory (UL) and the International Electrotechnical Commission (IEC) each have published electrical safety data indicating that the human body requires 10× more amplitude to evoke a response for AC 10 KHz voltages vs. low frequency or DC voltages. At 100 KHz frequency, 100× higher amplitude is required for AC vs. DC, and 1 MHz frequencies are even more benign. Even AC frequencies as low as 1 KHz have higher thresholds of sensation that low frequency or DC currents. Hence, as long as the AC voltage source 3112 in FIG. 15 has a frequency substantially greater than 1 KHz, no sensation is expected at location 3109 even if the cathodic stimulation region 3105 and/or the anodic stimulation region 3106 are being fully stimulated. The alternating current at the stimulating electrode could be a sine wave, square wave, triangular wave or other periodic waveform. In addition, the periodic waveform could be slowly modulated upwards or downwards in amplitude without re-introducing the electric shock sensation. For example, an exponentially decaying waveform in FIG. 6A is an example of a slowly modulated sine wave wherein the modulation is a gradual exponential decay. Hence, the wearable in FIG. 3 could generate the alternating current needed at the stimulation electrode by replacing AC source 3112 in FIG. 15 with the field-generating coil 1207 in FIG. 2B, 1306 in FIG. 3C, 1207 in FIG. 8A and 1207 in FIG. 9A.

The locations 3107 and 3108 in FIG. 15 are also susceptible to shock sensation. In these two locations, respective return electrodes 3103 and 3104 can be designed with a large enough electrical contact area to bring the current density at locations 3107 and 3108 to an arbitrarily low level. In the embodiments of this invention, the electrical contact area of these electrodes 3103 and 3104 will be sufficiently large so as to not excite the nerve endings in regions 3107 and 3108.

The electrical contact area of electrode 3102 can be smaller since its nerve endings under the skin are protected by AC current. Without limitation, electrode 3102 can have many electrode contact areas, and typically larger surface areas are more efficient for deeper stimulation targets and smaller surface areas are more efficient for shallower stimulation targets.

In summary for the invention in FIG. 15, a highly-targeted stimulating region 3105 is achieved well below the skin, and shock sensation is eliminated at locations 3107, 3108, 3109 just under the three electrodes 3103, 3104, 3102 respectively.

One assumption in FIG. 15 is that the cathodic current 3114 is roughly equal in magnitude to the anodic current 3113, but opposite in polarity. If these two magnitudes are not equal, then region 3109 would be net cathodic or net anodic, either of which could stimulate the nerve endings at 3109 and cause electric shock sensation. If the two currents in return electrodes 3113 and 3114 are not balanced, or roughly equal in magnitude naturally, then a number of balancing means could correct the imbalance: a cancelling DC bias could be introduced to the AC voltage source 3112, the electrode contact area of either electrode 3103 or 3104 could be increased or decreased to balance the anodic and cathodic currents, or a series resistor could be inserted in the wire entering electrode 3103 or in the wire entering electrode 3104. Without limitation, a microprocessor could sense the current levels to electrodes 3103 and 3104 by using current sensors, not shown in FIG. 15, and compute the imbalance and automatically and possibly dynamically control the balancing means described by adjusting parameters described above. Again, without limitation, such microprocessor could continually sense the anodic and cathodic currents and turn off the device when they are out of balance by an undesirable amount in response to an unintended condition.

Figure 16:
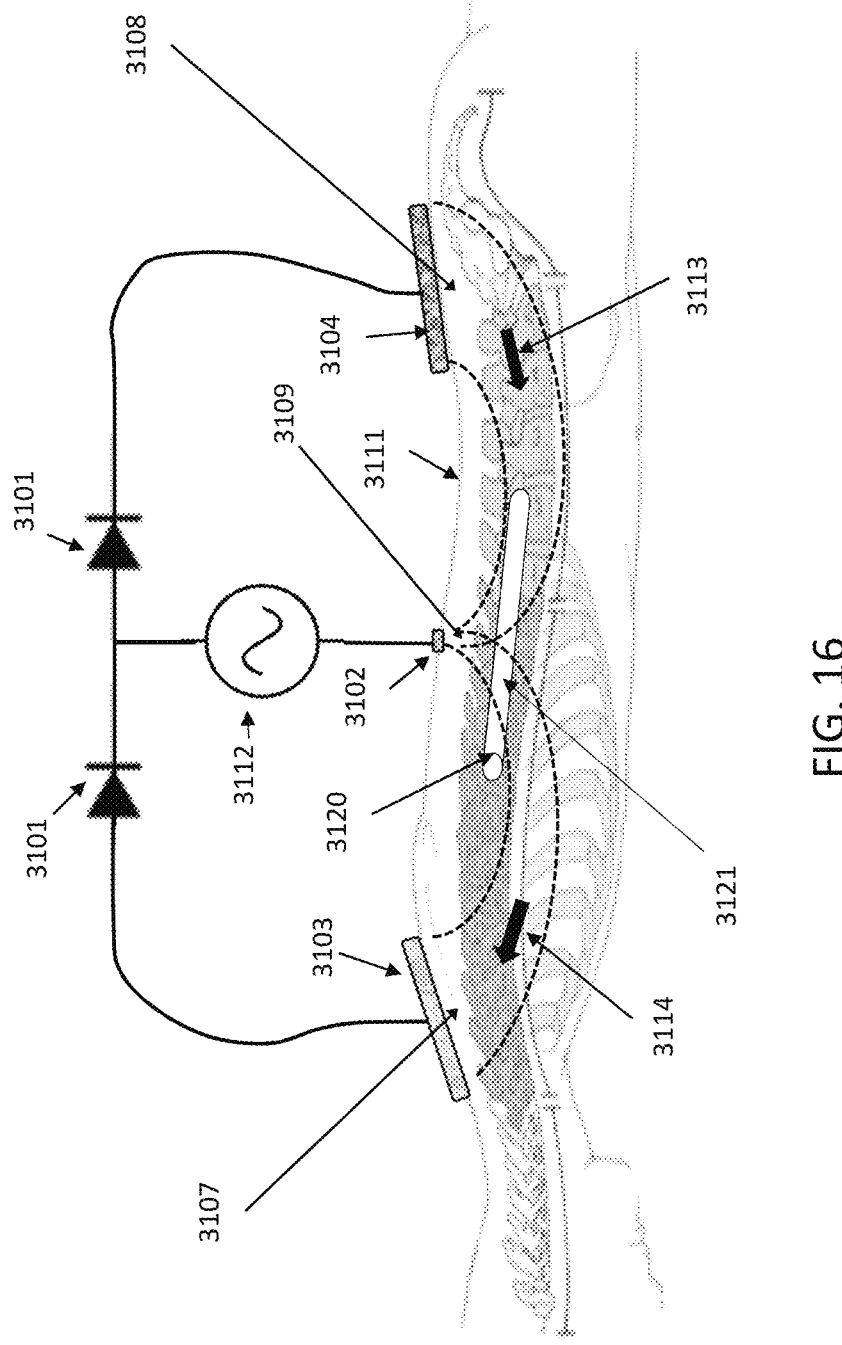
FIG. 16 shows the corresponding TENS system applied to the spinal cord.

FIG. 16 shows a similar configuration of the invention as FIG. 15, but this time applied to spinal cord stimulation (SCS). SCS is used extensively to treat lower back pain and other types of chronic pain by blocking the pain signals to the brain at the spinal cord. Because the spinal cord is 2-4 cm deep within the body, it is essentially impossible to achieve SCS treatment with TENS devices because the electric shock experienced at the skin electrodes would be intolerable when the current density is high enough for therapy at the spinal cord. In FIG. 16, location 3121 along the spinal cord 3120 is the target location. Although the target location is deep, the tissue between the skin 3111 and the spinal cord 3120 is mostly bone which is very resistive compared to other tissues. Hence, the current flowing in/out of electrode 3102 will preferentially and desirably flow between the vertebra to the more highly conductive tissues of the spinal cord.

Example 1: Improved TENS for the Median Nerve
and Carpal Tunnel Syndrome

Figure 17:
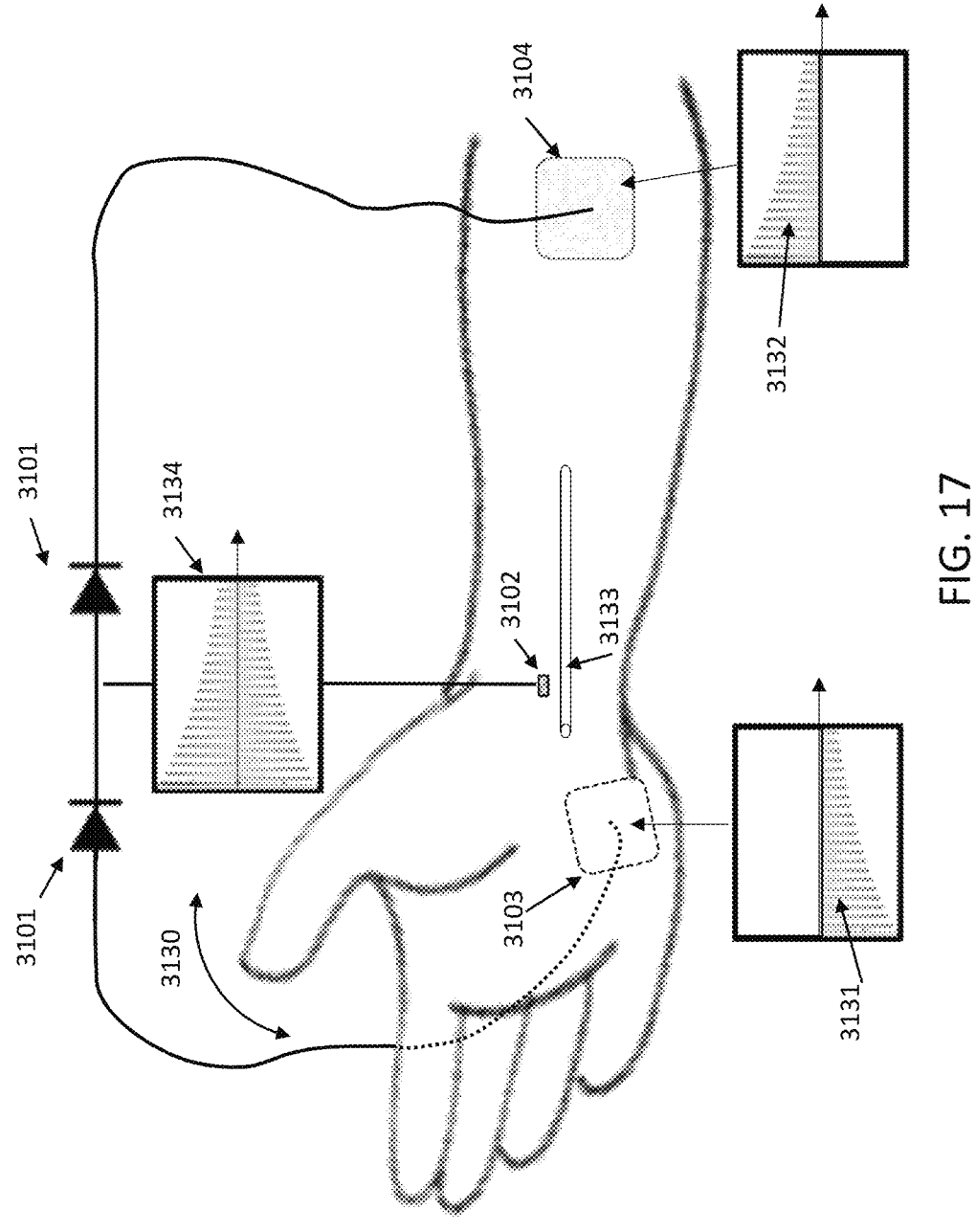
FIG. 17 shows the corresponding TENS system applied to the median nerve.

FIG. 17 shows the invention used to stimulate the median nerve 3133 of a human subject, which runs centrally along the forearm through the wrist to the hand. This nerve is often stimulated as therapy for carpal tunnel syndrome. Smaller electrode 3102 is placed just above the median nerve on the skin, and the two return electrodes 3103 and 3104 are placed on opposite sides of 3102, with 3103 placed on the reverse side of the hand. The voltage source 3134 generates one burst per second of an exponentially decaying AC sinusoid. The AC frequency of voltage source 3134 is 100 KHz, the decay time constant is 25 microseconds, and the peak amplitude is 200 volts. The result is about 6 milliamps of current peak at source 3134. The RMS voltage at electrodes 3103 and 3104 is about 66 volts during the burst. This RMS amplitude is typical for TENS devices. The cathodic negative pulses 3131 flow from electrode 3102 to electrode 3103 and anodic positive pulses 3132 to electrode 3104. The target stimulation is along the median nerve slightly anterior to electrode 3102.

With this invention configuration and stimulation parameters, the thumb of the human subject 3130 moved back and forth synchronously with the bursts of decaying sinusoids. The pain level experienced by the subject from any residual electric shock sensation was 1 (barely noticeable) on a scale from 0 to 10 where 0 is no pain and 10 is unspeakable pain.

Next, the same human subject had a prior art TENS device (the HNS 12 manufactured by B Braun Medical (Bethlehem, PA), not shown in FIG. 3) with the return electrode placed at location 3103 in FIG. 3, and the stimulating electrode placed at location 3102. Both prior-art electrodes had similar surface areas as invention electrodes, and the amplitude was increased to achieve the same thumb response as 3130 in FIG. 17. Using the prior-art TENS device, the human subject reported a pain level of 6 (moderately strong and could interfere with normal activities).

Hence, the invention TENS achieved the same response as the prior art TENS, but the pain level due to the electric shock sensation was reduced from 6 to 1.

Another nerve nearby the median nerve in FIG. 17 is the ulnar nerve. Stimulating of this nerve in a similar manner could relieve pain signals travelling on the ulnar nerve. Pain from cubital tunnel syndrome could be relieved this way, for example.

Although examples were just given for two types of pain signaled to the brain by the median and ulnar nerves, this invention can be applied to treat peripheral pain signaled by any peripheral nerve by affixing the electrodes to the appropriate location.

Example 2: Improved TENS for the Supraorbital Nerve and Migraine Headaches

Figure 18:
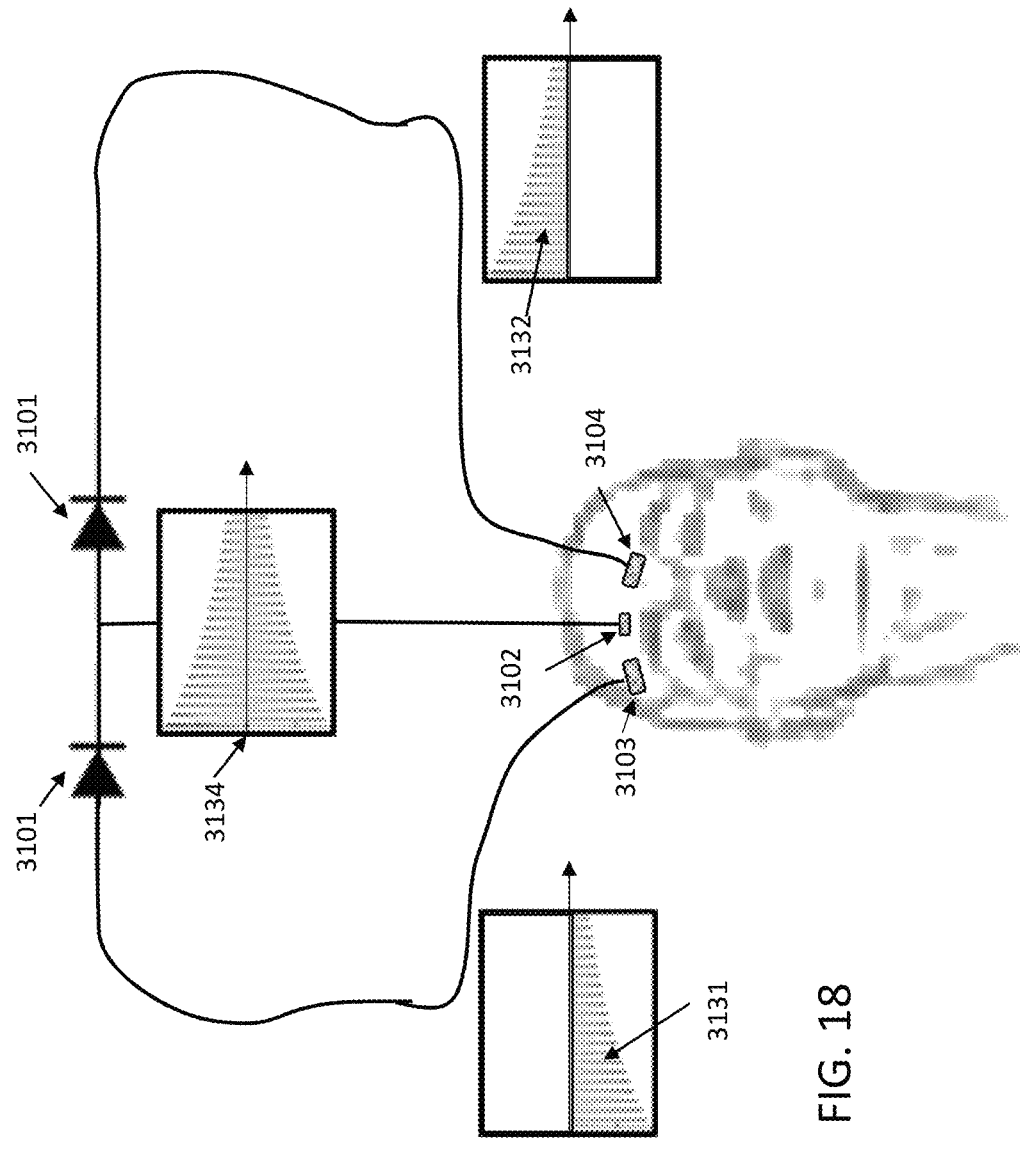
FIG. 18 shows the corresponding TENS system applied to the supra-orbital nerve.

FIG. 18 shows a similar configuration as FIG. 17, except that electrode 3102 was placed at the supraorbital nerve just above the midpoint of the eyebrow. This nerve is often stimulated as therapy for migraine headaches. The return electrodes 3103 and 3104 were placed two centimeters on either side of the stimulating electrode 3102. The system was operated similarly to the prior example with similar voltage amplitudes. For the human subject in this test, the pain from the migraine headaches was reduced from moderate to mild or from mild to none, depending on the evolution phase of the headache.

The same human subject also used the prior art TENS device available from Cefaly (Seraing, Belgium) during the same migraine episode. The prior art device also reduced the headache from moderate to mild or from mild to none. However, the pain level for the invention TENS was 1 and for the prior art TENS was 6 for supraorbital nerve stimulation, again a significant improvement for the invention vs. the prior art.

Figures 19A, 19B:
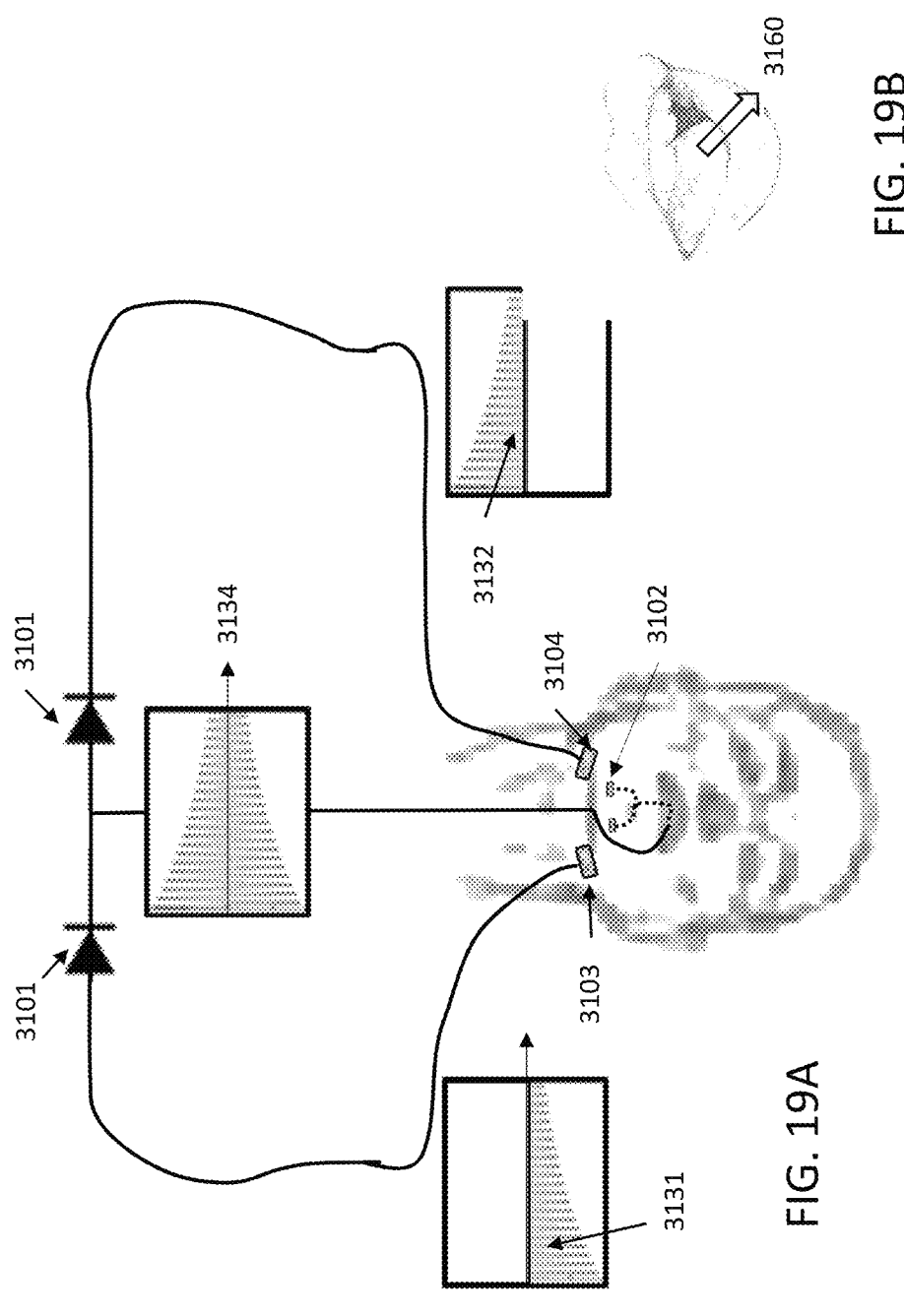
FIG. 19 shows the corresponding TENS system applied to the hypoglossal nerve.

Example 3 Improved TENS for the Hypoglossal Nerve and Obstructive Sleep Apnea Referring to FIG. 19A, the stimulating electrode was split into two electrodes 3102 electrically connected together, with one placed on either side of the lingual frenulum inside the mouth. The return electrodes 3103 and 3104 were placed under the jawbone on either side. Electrical stimulation at this location activates the genioglossus muscles and the hypoglossal nerve, which are located underneath the tongue. When contracted, these muscles pull the back of the tongue towards the mandible. The end result is protrusion of the tongue. This response was demonstrated in a human subject, with the tongue-protrusion response 3160 illustrated in FIG. 19B. As the invention was titrated up in stimulation amplitude to achieve significant protrusion of the tongue, comparable to Inspire Medical's implanted device, the human subject experienced a pain level of 1-2. Hence, the invention achieved the same response as a commercially available surgical implant, but with a device that is completely noninvasive. The configuration of the invention in FIG. 19A is ideal for treating obstructive sleep apnea (OSA).

In this description and examples, the invention was clearly shown to reduce electric shock sensation and associated pain and increase targeting of TENS stimulation. These improvements also enable higher stimulation intensities that are tolerable, directionally indicating higher efficacy of the invention vs. the prior art TENS devices. In addition, new treatments for non-invasive TENS devices such as spinal cord stimulation, might be possible for the first time with this invention.

Although the examples illustrating the invention and the human subject studies are for specific therapies, no limitation is implied of this invention being claimed for other known or currently unknown TENS therapies.

Although the present disclosure has been described in relation to various exemplary embodiments, various additional embodiments and alterations to the described embodiments are contemplated within the scope of the disclosure. Thus, no part of the foregoing description should be interpreted to limit the scope of the invention as set forth in the following claims. For all of the embodiments described above, the steps of the methods need not be performed sequentially.

I claim:

1. A neuromodulation system for obstructive sleep apnea, comprising:

a. an elongate device configured for injection about a hypoglossal nerve; the elongate device comprising:

a stimulating electrode;

a return electrode;

an elongated receiver coil;

a set of rectifying diodes;

a Zener diode, a resistor; and a capacitor; and wherein the elongate device does not contain a battery; and b. a wearable device comprising a field-generating coil connected to the capacitor and configured together to freely resonate during repetitive stimulations of the hypoglossal nerve;

wherein the elongate device is configured so that a voltage applied to the stimulating electrode is configured to be rectified by the rectifying diodes, to be limited by the Zener diode, and to average to zero before a start of a free resonance between the field-generating coil and the capacitor.

2. The neuromodulation system of claim 1, wherein the wearable device contains at least one button battery.

3. The neuromodulation system of claim 1, wherein the wearable device is configured to allow adjustment of an amplitude of stimulation by setting an initial electrical current flowing in the field-generating coil prior to the start of the free resonance.

4. The neuromodulation system of claim 3, wherein setting of the initial electrical current of the wearable device is based on the length of time that the field-generating coil is connected between a power supply and a ground.

5. The neuromodulation system of claim 1, wherein the set of rectifying diodes, the Zener diode, the resistor, the capacitor and any interconnections therebetween are coated with a moisture barrier with a thickness between 5 and 50 microns and comprising parylene or parylene C.

6. The neuromodulation system of claim 1 wherein the set of rectifying diodes, the Zener diode, the resistor, the capacitor and any interconnections therebetween are housed inside of a tube comprising polyimide or PEEK, the tube filled with biocompatible epoxy, and the tube is coated on the inside or the outside with a moisture barrier comprising parylene or parylene C.

7. The neuromodulation system of claim 1, wherein the stimulating and return electrodes are made from a biocompatible metal.

8. The neuromodulation system of claim 7, wherein the electrodes comprise platinum, iridium, or an alloy of platinum and iridium.

9. The neuromodulation system of claim 1, wherein the elongate device further comprises a tether attached to the elongate device at a location spaced apart from the stimulating electrode and configured for removability, the tether comprising polyester, polypropylene, ultrahigh molecular weight polyethylene, a tissue-absorbable synthetic material, or a combination thereof.

10. The neuromodulation system of claim 1 wherein the rectifying diodes are configured as a full-wave rectifier or a half wave rectifier.

11. The neuromodulation system of claim 1, further comprising an introducer needle, and wherein the elongate device is located inside the introducer needle, and a tip of the needle is configured to be electrically connected to a stimulation device.

12. The neuromodulation system of claim 1, further comprising: a sensor for sensing breathing motion, the sensor comprising:

a pouch;

a piezoelectric disk;

a support disk; and a pivot therebetween contained in the pouch;

wherein the support disk is located on a first side of the pouch configured for contact against a body of a user and wherein the piezoelectric disk is located on a second side of the pouch opposite the support disk, and is configured to be strapped toward the body.

13. The sensor of claim 12, wherein the sensor is electrically connected by a connector to the wearable device.

14. The sensor of claim 13, wherein the connector is a wire.

15. The sensor of claim 13, wherein the connector is a wireless link.

* * * * *